(12) United States Patent
Isabel et al.

(10) Patent No.: US 8,642,799 B2
(45) Date of Patent: Feb. 4, 2014

(54) CYSTEINE PROTEASE INHIBITORS FOR THE TREATMENT OF PARASITIC DISEASES

(71) Applicants: Elise Isabel, Point-Claire (CA); Christopher Mellon, L'Ile Bizard (CA); Christian Beaulieu, Laval (CA)

(72) Inventors: Elise Isabel, Point-Claire (CA); Christopher Mellon, L'Ile Bizard (CA); Christian Beaulieu, Laval (CA)

(73) Assignee: Merck Canada Inc., Quebec (CA)

( * ) Notice: Subject to any disclaimer, the term of this patent is extended or adjusted under 35 U.S.C. 154(b) by 0 days.

(21) Appl. No.: 13/861,046

(22) Filed: Apr. 11, 2013

(65) Prior Publication Data

US 2013/0244962 A1    Sep. 19, 2013

Related U.S. Application Data

(63) Continuation of application No. 12/745,070, filed as application No. PCT/CA2008/002071 on Nov. 26, 2008, now abandoned.

(60) Provisional application No. 61/004,747, filed on Nov. 29, 2007.

(51) Int. Cl.
*C07C 255/04*    (2006.01)
*A61K 31/275*    (2006.01)

(52) U.S. Cl.
USPC ........... 558/392; 558/413; 564/162; 564/163; 514/520; 514/521; 514/522; 514/618; 514/619

(58) Field of Classification Search
USPC ........... 558/392, 413; 564/162, 163; 514/520, 514/521, 522, 618, 619
See application file for complete search history.

(56) References Cited

U.S. PATENT DOCUMENTS

| 6,562,842 B2 | 5/2003 | Yamashita |
| 2003/0232863 A1 | 12/2003 | Bayly et al. |
| 2009/0264479 A1 | 10/2009 | Black et al. |
| 2010/0305056 A1 | 12/2010 | Isabel et al. |

FOREIGN PATENT DOCUMENTS

| CA | 2 477 657 A1 | 2/2003 |
| EP | 1 200 457 B1 | 8/2004 |
| WO | 99/53039 A1 | 10/1999 |
| WO | 00/09653 A2 | 2/2000 |
| WO | 03/075836 A2 | 9/2003 |
| WO | 2004/110988 A1 | 12/2004 |
| WO | 2007/012180 A1 | 2/2007 |

OTHER PUBLICATIONS

McKerrow et al., 1999, "Cysteine Protease Inhibitors as Chemotherapy for Parasitic Infections" Biorganic & Medicinal Chemistry 7:639-644.
Sajid et al., 2002, "Cysteine Proteases of Parasitic Organisms" Molecular Biochemical Parasitology120:1-21, 120.
von Oettingen, 2008, "High-yield Amplificaiton of *Cryptosporidium parvum* in Interferon Gamma Receptor Knockout Mice" Parasitology 135:1151-1156.

*Primary Examiner* — Shailendra Kumar
(74) *Attorney, Agent, or Firm* — Alysia A. Finnegan; Sheldon O. Heber

(57) ABSTRACT

Several parasites responsible for mammalian diseases are dependent on cysteine protease for various life-cycle functions. Inhibition or decreasing function of these proteases can be useful in the treatment and/or prevention of these parasitic diseases including; toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis or cestodiasis.

12 Claims, No Drawings

CYSTEINE PROTEASE INHIBITORS FOR THE TREATMENT OF PARASITIC DISEASES

This application is a continuation of U.S. patent application Ser. No. 12/745,070 filed May 27, 2010, now abandoned, which is the national stage entry of PCT International Application No. PCT/CA2008/002071 with an international filing date of 26 Nov. 2008, and claims the benefit of U.S. Provisional Application No. 61/004,747 filed Nov. 29, 2007.

BACKGROUND OF THE INVENTION

Several parasites responsible for mammalian diseases are dependent on cysteine protease for various life-cycle functions Inhibition of these proteases can be useful in the treatment and/or prevention of these parasitic diseases, see Lecaille, F., et al, Chem. Rev., 102, 4459-4488, 2002.

Cruzipain is a cysteine protease enzyme present in *Trypanosoma cruzi* and is thought to play an important role in all stages of the parasite's life cycle. The enzyme is highly expressed in the epimastigote stage where it is primarily a lysosomal enzyme and may be involved in protein digestion during differentiation to the infective metacyclic trypomastigote stage. Identification of cruzipain in the membrane of the trypomastigote implicates this enzyme in the penetration of the parasite into the host cell. Cruzipain is also found in the membranes of the amastigote form of the parasite, see Cazzulo, J. J., et al, Current Pharmaceutical Design, 7, 1143-1156, 2001. Cruzipain efficiently degrades human IgG, which may play a protective role for the parasite by preventing antigen presentation and thus reducing the host immune response. Based on these observations, it has been proposed that cruzipain is a valid drug target for chemotherapy of Chagas disease. Cruzipain has been reported to exist in at least two polymorphic sequences, known as cruzipain 1 and cruzipain 2, both of which may be involved in the viability of *Trypanosoma cruzi* (Lima, et al, Molecular & Parasitology 114, 41-52, 2001).

The use of cysteine protease inhibitors for the treatment of Chagas disease and African trypanosomaisis has been shown by the observation that irreversible inhibitors of cruzipain can cure Chagas disease in mouse models, see Engel, J., et al, J. Exp. Chem., 188, 725-734, 1998.

A similar role for the cysteine protease trypanopain-Tb has been proposed in the life-cycle of *Trypanosoma brucei*, the parasite responsible for African trypanosomaisis, or sleeping sickness.

A similar parasite, *T. congolense*, is responsible for the bovine disease trypanosomiasis. Congopain is the analogous cysteine protease to cruzipain in this parasite.

Falcipain is an important cysteine protease in *Plasmodium falicparum*. This enzyme is reported to be important in the degradation of host hemoglobin in parasite food vacuoles. The processing of hemoglobin is essential to the growth of the parasite, thus an inhibitor of falcipain should be useful as a treatment for malaria.

Two cysteine proteases, SmCL1 and SmCL2, are present in the human blood fluke *Schistosoma mansoni*. SmCL1 may play a role in the degradation of host hemoglobin, while SmCL2 may be important to the reproductive system of the parasite (Brady, C. P., et al, Archives of Biochemistry and Biophysics, 380, 46-55, 2000) Inhibition of one or both of these proteases may provide an effective treatment for human schistosomiasis.

LmajcatB and CP2.8ΔCTE are important cysteine proteases of the parasitic protazoa *Leishmania major* and *Leishmania mexicanus* respectively, see Alves, L. C., et al, Eur. J. Biochem, 268, 1206-1212, 2001 Inhibition of these enzymes may provide a useful treatment for leishmaniasis.

CP2 is a major cysteine protease of the flagellate *Giardia lamblia* which may be important to encystation and replication of the parasite (DuBois, K. N. et al, J. Biol. Chem., 283, 18024-18031, 2008) Inhibition of CP2 or the other 26 known clan CA protease in this parasite may provide a useful treatment of giardiasis.

Two cysteine proteases coded by AcCP-1 and AcCP-2 have been found in the hookworm *Ancylostoma caninum* (Harrop, S. A. et al, Mol Biochem Parasitol. 71, 163-71, 1995. Inhibition of these proteases may provide a useful treatment of *Ancyclostoma* infection.

Cysteine proteases are also known to be present in Trichomonas vaginalis (Jane R. Schwebke, J. R. and Burgess D., Clinical Microbiology Reviews, 17, 794-803, 2004.). Inhibition of these proteases may provide a treatment for the venereal disease trichomoniasis associated with this parasite.

*Entamoeba histolytica* is the protozoan causative agent of human amoebiasis. It is known to contain the cysteine protease EhCP112 (Garcia-Rivera, G. et al, Molecular Microbiology 33, 556-568, 1999). Use of a protease inhibitor may be useful in the treatment of amoebiasis.

A cysteine protease has been identified in the intestinal parasite *Cryptosporidium parvum* (Nesterenko M. W. et al, Microbios 83, 77-88 1995, Formey J. R. et al, *J. Parasitol.* 82, 889-92, 1996). A cysteine protease inhibitor could be a useful treatment of cryptosporidiosis. Indeed, treatment of mice with the irreversible inhibitor K-777 results in clearance of the parasite from immunocompromised mice (Ndao et al, Parasitology 2008 135, 1151-6, 2008).

A number of Eimeria parasites can lead to disease in animals of agricultural importance such as chickens and cattle (Barta. J. R. et al, J. Parasitol. 83, 262-71, 1997). Cysteine protease inhibitors may provide a treatment for mammals infected with *E. bovis, E. necatrix, E. tenella, E. mitis, E. mivati, E. praecox, E. maxima, E. brumetti*, and *E. acervuline*

Numerous other parasites have been reported to be dependent on cysteine proteases (Sajid, M., and McKerrow, J. H. *Molecular and Biochemical Parasitology*, 120, 1-21, 2002) and thus may be treated with inhibitors of these proteases. These parasites include *Plasmodium chabaudi, Plasmodium Berghei, Naegleria fowleri, Theileria parva, Toxoplasma gondii, Strongyloides stercoralis, Ascaris suum, Haemonchus contortus, Necator americanus, Taenia saginata, Gymnorhynchus gigas, Spirometra mansonoidese, Diplostomum pseudospathaceum, Onchercerca volvulus, Fasciaola hepatica* and *Dilofilaria immitis*.

The present invention relates to compounds that are capable of treating and/or preventing mammalian parasitic diseases in which the parasite utilizes a critical cysteine protease from the papain family.

SUMMARY OF THE INVENTION

The present invention relates to compounds capable of treating and/or preventing parasitic disease. Examples or parasitic diseases include toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis.

One embodiment of the present invention is illustrated by a compound of Formula I, and the pharmaceutically acceptable salts and stereoisomers thereof:

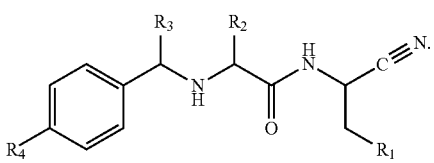

DETAILED DESCRIPTION OF THE INVENTION

The present invention relates to compounds that inhibit or decrease the activity of cruzipain. Because cruzipain is needed for various life-cycle functions of the parasite *Trypanosoma cruzi*, compounds of the invention are useful for inhibiting and/or decreasing the growth and/or survivial of *Trypanosoma cruzi*. Thus, parasitic disease caused by *Trypanosoma cruzi* can be treated and/or prevented by administering compounds of the invention to patients in need thereof.

Additionally, other parasitic diseases caused by parasites that use cruzipain or similar cysteine proteases for life-cycle functions can also be treated and/or prevented by administration of the compounds of the present invention.

Compounds of the present invention are capable of treating and/or preventing parasitic disease. Examples of parasitic diseases include, but are not limited to, toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis.

One embodiment of the present invention is illustrated by a compound of the following formula, and the pharmaceutically acceptable salts and stereoisomers thereof:

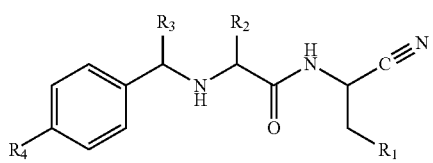

I wherein $R^1$ is aryl or heteroaryl optionally substituted with one, two or three substituents independently selected from $C_{1-6}$ alkyl, —$COOR^5$, halo, haloalkyl, cyano, aryl, heteroaryl or —$SO_m(C_{1-6}$ alkyl);
$R^2$ is $C_{1-6}$ alkyl, $C_{3-6}$ cycloalkyl wherein said alkyl group is optionally substituted with $C_{3-6}$ cycloalkyl or one to six halo;
$R^3$ is $C_{1-6}$ alkyl substituted with one to six halo;
$R^4$ is halo, aryl, heteroaryl, arylalkyl, heteroarylalkyl or heterocyclyl wherein said $R^4$ aryl, $R^4$ heteroaryl, $R^4$ arylalkyl or $R^4$ heteroarylalkyl groups are optionally substituted with one, two, or three substituents independently selected from halo, $C_{1-6}$ alkyl, $C_{1-6}$ haloalkyl, $C_{1-6}$ hydroxyalkyl, $C_{1-6}$ halo hydroxyalkyl, alkoxy, haloalkoxy, cyano, aryl, aryl-$SO_2CH_3$, heteroaryl, arylalkyl, heteroarylalkyl, heterocyclyl, —$SO_m(C_{1-6}$ alkyl), —$SO_2NR^6R^7$, —$COOR^5$, —$CONR^6R^7$ and $C_{3-6}$ cycloalkyl-$R^8$;
$R^5$ is hydrogen or $C_{1-6}$ alkyl;
$R^6$ is hydrogen, $C_{1-6}$ alkyl, $C_2$-$C_6$ alkene, ($C_{1-6}$ alkyl)aryl, $C_{1-6}$ hydroxyalkyl, —$O(C_{1-6}$ alkyl), hydroxyl, aryl, heteroaryl, $C_{3-8}$ cycloalkyl, heterocyclyl, $C_{1-6}$ alkyl-$COOR^5$, $C_{0-6}$ alkyl-$C(O)NH_2$, wherein said alkyl, aryl, heteroalkyl, $C_{3-8}$ cycloalkyl and heterocyclyl can be optionally substituted on either the carbon or the heteroatom with one, two or three substituents independently selected from $C_{1-6}$ alkyl or halo;
$R^7$ is hydrogen, $C_{1-6}$ alkyl, ($C_{1-6}$ alkyl)aryl, $C_{1-6}$ hydroxyalkyl, —$O(C_{1-6}$ alkyl), hydroxyl, aryl, heteroaryl, $C_{3-8}$ cycloalkyl, heterocyclyl, wherein said alkyl, aryl, heteroaryl, $C_{3-8}$ cycloalkyl and heterocyclyl can be optionally substituted on either the carbon or the heteroatom with one, two, or three substituents independently selected from $C_{1-6}$ alkyl or halo;
$R^6$ and $R^7$ can be taken together with the nitrogen atom to which they are attached to form a $C_{3-8}$ heterocyclyl ring wherein said 3-8 membered ring system may be optionally substituted with one or two substituents independently selected from $C_{1-6}$ alkyl and halo;
$R^8$ is either H, $C_{1-6}$ alkyl, $C_{1-6}$ haloalkyl, $C_{1-6}$ hydroxyalkyl, $C_{1-6}$ halo hydroxyalkyl, alkoxy, haloalkoxy, cyano, heteroaryl, arylalkyl, heteroarylalkyl, heterocyclyl, —$SO_2CH_3$, —$SO_2NR^6R^7$, —$SO_m(C_{1-6}$ alkyl), —$COOR^5$ or —$CONR^6R^7$;

wherein m is an integer from zero to two.

In an embodiment, $R^1$ is pyridine, pyridine N-oxide or phenyl wherein the said phenyl may be substituted in ortho and/or para position with 1-3 substituents independently selected from bromo, fluoro, chloro, cyano, trifluoromethyl, methyl sulfone, pyridine or pyridine-N-oxide and phenyl. In a specific embodiment, $R^1$ is phenyl. The other variables are provided for as originally defined.

In another embodiment, $R^2$ is dichloroethyl, 2,2-fluoromethyl propyl, methylenecyclopropyl, cyclopropyl, 2-methyl propyl or isopropyl. The other variables are as originally defined or as provided for in the previous embodiments.

In another embodiment, $R^3$ is trifluoromethyl. The other variables are as originally defined or as provided for in any of the previous embodiments.

In another embodiment, $R^4$ is bromo, methylpyrazole, N-methylpyrrole, pyridine, pyridine N-oxide or phenyl wherein the said phenyl maybe optionally disubstituted with chloro in ortho position and —$SO_2Me$ in para position or monosubstituted in para position with —$SO_2Me$, —$SO_2NH_2$, piperazine, 2,2-difluoroethanol, —SMe, —SOMe, pyridine, pyridine N-oxide, 2-methylpropane-1-ol, methyl-pyrazole, 4-$SO_2Me$-phenyl or cyclopropyl wherein the said cyclopropyl may be substituted with oxadiazole, —$CONR^6R^7$, —$COOR^5$, cyano or phenyl substituted in the para position with —$SO_2Me$. The other variables are as originally defined or as provided for in any of the previous embodiments.

In another embodiment, $R^5$ is hydrogen. The other variables are as originally defined or as provided for in any of the previous embodiments.

In another embodiment, $R^6$ and $R^7$ are independently hydrogen, ethanol, allyl, cyclopropyl, —$CH_2CONH_2$, 1,1,1-trifluoroethane, methylacetate or $R^6$ and $R^7$ are forming a morpholine ring. The other variables are as originally defined or as provided for in any of the previous embodiments.

Another class of compounds of the present invention is illustrated by a compound of the following formula, and the pharmaceutically acceptable salts and stereoisomers thereof:

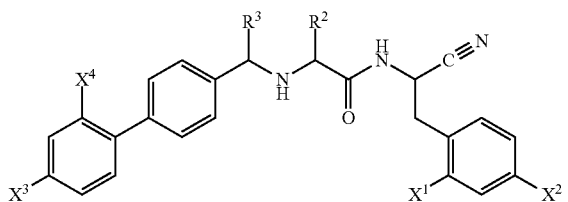

wherein $X^1$ is hydrogen or halo;
$X^2$ is hydrogen, cyano, chloro or $C_{1-6}$ haloalkyl;
$R^2$ is $C_{1-6}$ haloalkyl;
$R^3$ is $C_{1-6}$ haloalkyl;
$X^3$ is hydrogen, —$SO_m(C_{1-6}$ alkyl) or heterocyclyl;
$X^4$ is hydrogen or halo;
m is an integer from zero to two.

In another embodiment, $X^1$ is fluoro or chloro. The other variables are provided for as originally defined for Structure II.

In another embodiment, $X^2$ is cyano or trifluoromethyl. The other variables are as originally defined or as provided for in the previous embodiments for Structure II.

In another embodiment, $R^2$ is dichloroethyl or 2,2-fluoromethyl propyl. The other variables are as originally defined or as provided for in any of the previous embodiments for Structure II.

In another embodiment, $R^3$ is trifluoromethyl. The other variables are as originally defined or as provided for in any of the previous embodiments for Structure II.

In another embodiment, $X^3$ is methylsulfone or piperazine. The other variables are as originally defined or as provided for in any of the previous embodiments for Structure II.

In another embodiment, $X^4$ is methyl. The other variables are as originally defined or as provided for in any of the previous embodiments for Structure II.

Reference to the preferred embodiments set forth above is meant to include all combinations of particular and preferred groups unless stated otherwise.

Specific embodiments of the papain family cysteine protease inhibitors of the present invention include, but are not limited to:

(2S)-4,4-dichloro-N-[(1S)-1-cyano-2-(4-cyano-2-fluorophenyl)ethyl]-2-({(1S)-2,2,2-trifluoro-1-[4'-(methylsulfonyl)biphenyl-4-yl]ethyl}amino)butanamide;

N-[(1S)-1-cyano-2-(4-cyanophenyl)ethyl]-4-fluoro-$N^2$-{(1S)-2,2,2-trifluoro-1-[4'-(methylsulfonyl)biphenyl-4-yl]ethyl}-L-leucinamide;

N-[(1S)-1-cyano-2-(4-cyano-2-fluorophenyl)ethyl]-4-fluoro-$N^2$-{(1S)-2,2,2-trifluoro-1-[4'-(methylsulfonyl)biphenyl-4-yl]ethyl}-L-leucinamide;

N-[(1R)-1-cyano-2-(4-cyano-2-fluorophenyl)ethyl]-4-fluoro-$N^2$-{(1S)-2,2,2-trifluoro-1-[4'-(methylsulfonyl)biphenyl-4-yl]ethyl}-L-leucinamide;

N-[2-(2-chloro-4-cyanophenyl)-1-cyanoethyl]-4-fluoro-$N^2$-{(1S)-2,2,2-trifluoro-1-[4'-(methylsulfonyl)biphenyl-4-yl]ethyl}-L-leucinamide;

N-[2-(2-chloro-4-cyanophenyl)-1-cyanoethyl]-$N^2$-{(1S)-1-[2'-chloro-4'-(methylsulfonyl)biphenyl-4-yl]-2,2,2-trifluoroethyl}-4-fluoro-L-leucinamide;

N~2~-{(1S)-1-[2'-chloro-4'-(methylsulfonyl)biphenyl-4-yl]-2,2,2-trifluoroethyl}-N-[1-cyano-2-(4-cyano-2-fluorophenyl)ethyl]-4-fluoro-L-leucinamide;

N-[1-cyano-2-(4-cyano-2-fluorophenyl)ethyl]-4-fluoro-$N^2$-{(1S)-2,2,2-trifluoro-1-[4'-(methylsulfonyl)biphenyl-4-yl]ethyl}-L-leucinamide;

N-[1-cyano-2-(4-cyanophenyl)ethyl]-$N^2$—N{(1S)-2,2,2-trifluoro-1-[4'-(methylsulfonyl)biphenyl-4-yl]ethyl}-L-leucinamide;

N-{(1S)-1-cyano-2-[4-(trifluoromethyl)phenyl]ethyl}-4-fluoro-$N^2$-{(1S)-2,2,2-trifluoro-1-[4'-(methylsulfonyl)biphenyl-4-yl]ethyl}-L-leucinamide;

(S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-2-ylmethyl)-methyl]-amide (S)-4-Fluoro-4-methyl-2-[(S)-2,2,2-trifluoro-1-(4'-methanesulfonyl-biphenyl-4-yl)-ethylamino]-pentanoic acid ((S)-cyano-pyridin-3-ylmethyl-methyl)-amide (S)—N—((S)-Benzyl-cyano-methyl)-3-cyclopropyl-2-[(S)-2,2,2-trifluoro-1-(4'-methanesulfonyl-biphenyl-4-yl)-ethylamino]-propionamide (S)—N—[(S)-Cyano-(2-fluoro-4-trifluoromethyl-benzyl)-methyl]-3-methyl-2-[(S)-2,2,2-trifluoro-1-(4'-methanesulfonyl-biphenyl-4-yl)-ethylamino]-butyramide (S)—N—[(S)-Cyano-(2-fluoro-4-trifluoromethyl-benzyl)-methyl]-2-{(S)-1-[4'-((R)-2,2-difluoro-1-hydroxy-ethyl)-biphenyl-4-yl]-2,2,2-trifluoro-ethylamino}-3-methyl-butyramide (S)-4-Fluoro-4-methyl-2-[(S)-2,2,2-trifluoro-1-(4'-methanesulfonyl-biphenyl-4-yl)-ethylamino]-pentanoic acid ((S)-cyano-pyridin-4-ylmethyl-methyl)-amide 1-{4'-[(S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid (2-hydroxy-ethyl)-amide 1-{4'-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid amide 1-{4'-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid (S)—N—[(S)-Cyano-(4-cyano-2-fluoro-benzyl)-methyl]-2-{(S)-1-[4'-((R)-2,2-difluoro-1-hydroxy-ethyl)-biphenyl-4-yl]-2,2,2-trifluoro-ethylamino}-3-methyl-butyramide 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid allylamide 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid cyclopropylamide 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid carbamoylmethyl-amide 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid (2,2,2-trifluoro-ethyl)-amide ({1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarbonyl}-amino)-acetic acid methyl ester 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid (2-hydroxy-ethyl)-amide (S)—N—[(S)-Cyano-(4-cyano-2-fluoro-benzyl)-methyl]-3-methyl-2-[(S)-2,2,2-trifluoro-1-(4'-methanesulfonyl-biphenyl-4-yl)-ethylamino]-butyramide (S)—N—[(S)-Cyano-(4-cyano-2-fluoro-benzyl)-methyl]-3-methyl-2-[(S)-2,2,2-trifluoro-1-(4'-methanesulfonyl-biphenyl-4-yl)-ethylamino]-butyramide (S)—N—((S)-Benzyl-cyano-methyl)-2-{(S)-1-[4'-((R)-2,2-difluoro-1-hydroxy-ethyl)-biphenyl-4-yl]-2,2,2-trifluoro-ethylamino}-3-methyl-butyramide (S)—N—((S)-Benzyl-cyano-methyl)-3-methyl-2-[(S)-2,2,2-trifluoro-1-(4-pyridin-4-yl-phenyl)-ethylamino]-butyramide 1-[4'-((S)-1-{(S)-1-[((S)-Benzyl-cyano-methyl)-carbamoyl]-2-methyl-propylamino}-2,2,2-trifluoro-ethyl)-biphenyl-4-yl]-cyclopropanecarboxylic acid amide 4-[4'-((S)-1-{(S)-1-[((S)-Benzyl-cyano-methyl)-carbamoyl]-2-methyl-propylamino}-2,2,2-trifluoro-ethyl)-biphenyl-4-yl]-piperazin-1-ium; chloride (S)-4-Fluoro-4-methyl-2-[(S)-2,2,2-trifluoro-1-(4'-methanesulfonyl-biphenyl-4-yl)-ethylamino]-pentanoic acid [(S)-cyano-(2-fluoro-4-trifluoromethyl-benzyl)-methyl]amide (S)-4-Fluoro-4-methyl-2-{(S)-2,2,2-trifluoro-1-[4'-(1-oxypyridin-4-yl)-biphenyl-4-yl]-ethylamino}-pentanoic acid ((S)-1-cyano-2-phenyl-ethyl)-amide (S)-2-[(S)-1-(4-Bromo-phenyl)-2,2,2-trifluoro-ethylamino]-4-fluoro-4-methyl-pentanoic acid [(S)-1-cyano-2-(4-cyano-2-fluoro-phenyl)-ethyl]-amide (S)-4-Fluoro-4-methyl-2-((S)-2,2,2-trifluoro-1-{4'-[1-(morpholine-4-carbonyl)-cyclopropyl]-biphenyl-4-yl}-ethylamino)-pentanoic acid [(S)-1-cyano-2-(4-cyano-2-fluoro-phenyl)-ethyl]-amide (S)-4-Fluoro-4-methyl-2-{(S)-2,2,2-trifluoro-1-[4'-(2-hydroxy-2-methyl-propyl)-biphenyl-4-yl]-ethylamino}-pentanoic acid [(S)-1-cyano-2-(4-cyano-2-fluoro-phenyl)-ethyl]-amide (S)—N—((S)-1-Cyano-2-phenyl-ethyl)-3-methyl-2-[(S)-2,2,2-trifluoro-1-(4'-methanesulfonyl-biphenyl-4-yl)-ethylamino]-butyramide (S)-2-[(S)-1-(4-Bromo-phenyl)-2,2,2-trifluoro-ethylamino]-N—((S)-1-cyano-2-phenyl-ethyl)-3-methyl-butyramide (S)-4-Fluoro-4-methyl-2-[(S)-2,2,2-trifluoro-1-(4'-pyridin-4-yl-biphenyl-4-yl)-ethylamino]-pentanoic acid [(S)-1-cyano-2-(4-cyano-2-fluoro-phenyl)-ethyl]-amide 1-[4'-((S)-1-{(S)-1-[(S)-1-Cyano-2-(4-cyano-2-fluoro-phenyl)-ethylcarbamoyl]-3-fluoro-3-methyl-butylamino}-2,2,2-trifluoro-ethyl)-biphenyl-4-yl]-cyclopropanecarboxylic acid amide (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [cyano-(2-fluoro-4-trifluoromethyl-benzyl)-methyl]-amide (S)-4-Fluoro-4-methyl-2-[(S)-2,2,2-trifluoro-1-(4'-pyridin-4-yl-biphenyl-4-yl)-ethylamino]-pentanoic acid ((S)-1-cyano-2-phenyl-ethyl)-amide (S)-4-Fluoro-4-methyl-2-{(S)-2,2,2-trifluoro-1-[4-(1-methyl-1H-pyrrol-2-yl)-phenyl]-ethylamino}-pentanoic acid ((S)-1-cyano-2-phenyl-ethyl)-amide (S)-4-Fluoro-4-methyl-2-[(S)-2,2,2-trifluoro-1-(4'-methanesulfonyl-biphenyl-4-yl)-ethylamino]-pentanoic acid [cyano-(2,4-difluoro-benzyl)-methyl]-amide (S)-4-Fluoro-4-methyl-2-[(S)-2,2,2-trifluoro-1-(4'-methanesulfonyl-biphenyl-4-yl)-ethylamino]-pentanoic acid [cyano-(2-fluoro-4-trifluoromethyl-benzyl)-methyl]-amide (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [(S)-cyano-(4-cyano-2-fluoro-benzyl)-methyl]-amide (S)-4-Fluoro-4-methyl-2-[(S)-2,2,2-trifluoro-1-(4'-sulfamoyl-biphenyl-4-yl)-ethylamino]-pentanoic acid ((S)-1-cyano-2-phenyl-ethyl)-amide 1-(4'-{(S)-1-[(S)-1-((S)-1-Cyano-2-phenyl-ethylcarbamoyl)-3-fluoro-3-methyl-butylamino]-2,2,2-trifluoro-ethyl}-biphenyl-4-yl)-cyclopropanecarboxylic acid amide (S)-4-Fluoro-4-methyl-2-{(S)-2,2,2-trifluoro-1-[4'-(1-[1,2,4]oxadiazol-3-yl-cyclopropyl)-biphenyl-4-yl]-ethylamino}-pentanoic acid ((S)-1-cyano-2-phenyl-ethyl)-amide (S)-4-Fluoro-4-methyl-2-((S)-2,2,2-trifluoro-1-{4'-[1-(morpholine-4-carbonyl)-cyclopropyl]-biphenyl-4-yl}-ethylamino)-pentanoic acid ((S)-1-cyano-2-phenyl-ethyl)-amide (S)-2-{(S)-1-[4'-(1-Cyano-cyclopropyl)-biphenyl-4-yl]-2,2,2-trifluoro-ethylamino}-4-fluoro-4-methyl-pentanoic acid ((S)-1-cyano-2-phenyl-ethyl)-amide (S)-4-Fluoro-4-methyl-2-[(S)-2,2,2-trifluoro-1-(4'-methylsulfanyl-biphenyl-4-yl)-ethylamino]-pentanoic acid [(S)-1-cyano-2-(4-cyano-2-fluoro-phenyl)-ethyl]-amide (S)-4-Fluoro-4-methyl-2-[(S)-2,2,2-trifluoro-1-(4'-methanesulfinyl-biphenyl-4-yl)-ethylamino]-pentanoic acid [(S)-1-cyano-2-(4-cyano-2-fluoro-phenyl)-ethyl]-amide (S)-4-Fluoro-4-methyl-2-[(S)-2,2,2-trifluoro-1-(4-methanesulfonyl-[1,1';4',1"]terphenyl-4"-yl)-ethylamino]-pentanoic acid ((S)-benzyl-cyano-methyl)-amide (S)-4,4-Dichloro-N—[(S)-cyano-(4-cyano-2-fluoro-benzyl)-methyl]-2-[(S)-2,2,2-trifluoro-1-(4'-methanesulfonyl-biphenyl-4-yl)-ethylamino]-butyramide (S)—N-(Benzyl-cyano-methyl)-4,4-dichloro-2-[(S)-2,2,2-trifluoro-1-(4'-methanesulfonyl-biphenyl-4-yl)-ethylamino]-butyramide (2S)—N-[(1S)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide (S)-4-Fluoro-4-methyl-2-[(S)-2,2,2-trifluoro-1-(4'-methanesulfonyl-biphenyl-4-yl)-ethylamino]-pentanoic acid [2-(2-chloro-4-cyano-phenyl)-1-cyano-ethyl]-amide (S)-2-[(S)-1-(2'-Chloro-4'-methanesulfonyl-biphenyl-4-yl)-2,2,2-trifluoro-ethylamino]-4-fluoro-4-methyl-pentanoic acid [2-(2-chloro-4-cyano-phenyl)-1-cyano-ethyl]-amide (S)-2-[(S)-1-(2'-Chloro-4'-methanesulfonyl-biphenyl-4-yl)-2,2,2-trifluoro-ethylamino]-4-fluoro-4-methyl-pentanoic acid [1-cyano-2-(4-cyano-2-fluoro-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [1-cyano-2-(4-cyano-2-fluoro-phenyl)-ethyl]-amide (S)-2-[(S)-1-(4-Bromo-phenyl)-2,2,2-trifluoro-ethylamino]-4-methyl-pentanoic acid [(S)-1-cyano-2-(4-cyano-phenyl)-ethyl]-amide (S)-4-Methyl-2-[(S)-2,2,2-trifluoro-1-(4'-methanesulfonyl-biphenyl-4-yl)-ethylamino]-pentanoic acid [1-cyano-2-(4-cyano-phenyl)-ethyl]-amide (S)-2-[(S)-1-(4-Bromo-phenyl)-2,2,2-trifluoro-ethylamino]-4-methyl-pentanoic acid [(S)-1-cyano-2-(4-methanesulfonyl-phenyl)-ethyl]-amide (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [(S)-1-cyano-2-(4-methanesulfonyl-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-cyano-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-trifluoromethyl-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(2,4-dichloro-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(2-fluoro-phenyl)-ethyl]-amide (S)-4-Fluoro-4-methyl-2-[(S)-2,2,2-trifluoro-1-(4'-methanesulfonyl-biphenyl-4-yl)-ethylamino]-pentanoic acid [(S)-cyano-(4-fluoro-benzyl)-methyl]-amide 4-((S)-2-Cyano-2-{(S)-4-fluoro-4-methyl-2-[(S)-2,2,2-trifluoro-1-(4'-methanesulfonyl-biphenyl-4-yl)-ethylamino]-pentanoylamino}-ethyl)-benzoic acid ethyl ester (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-pyridin-3-yl-phenyl)-ethyl]-amide (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid ((S)-benzyl-cyano-methyl)-amide (S)-4-Fluoro-4-methyl-2-[(S)-2,2,2-trifluoro-1-(4'-methanesulfonyl-biphenyl-4-yl)-ethylamino]-pentanoic acid ((S)-benzyl-cyano-methyl)-amide (2S)—N-[(1R)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide (S)-4-Fluoro-4-methyl-2-[(S)-2,2,2-trifluoro-1-(4'-methanesulfonyl-biphenyl-4-yl)-ethylamino]-pentanoic acid [(S)-(4-bromo-2,6-difluoro-benzyl)-cyano-methyl]-amide (S)-4-Fluoro-4-methyl-2-[(S)-2,2,2-trifluoro-1-(4'-methanesulfonyl-biphenyl-4-yl)-ethylamino]-pentanoic acid [(S)-cyano-(4-cyano-2,6-difluoro-benzyl)-methyl]-amide (S)—N—[(S)-Cyano-(4-cyano-2-fluoro-benzyl)-methyl]-2-cyclopropyl-2-[(S)-2,2,2-trifluoro-1-(4'-methanesulfonyl-biphenyl-4-yl)-ethylamino]-acetamide (S)—N—[(S)-Cyano-(4-cyano-2-fluoro-benzyl)-methyl]-2-cyclopropyl-2-{(S)-1-[4'-((R)-2,2-difluoro-1-hydroxy-ethyl)-biphenyl-4-yl]-2,2,2-trifluoro-ethylamino}-acetamide (S)—N—-[S)-(4-Bromo-2,6-difluoro-benzyl)-cyano-methyl]-3-methyl-2-[(S)-2,2,2-trifluoro-1-(4'-methanesulfonyl-biphenyl-4-yl)-ethylamino]-butyramide (S)—N—-[(S)-(4-Bromo-2,6-difluoro-benzyl)-cyano-methyl]-2-{(S)-1-[4'-((R)-2,2-difluoro-1-hydroxy-ethyl)-biphenyl-4-yl]-2,2,2-trifluoro-ethylamino}-3-methyl-butyramide (S)—N—[(S)-Cyano-(4-cyano-2,6-difluoro-benzyl)-methyl]-3-methyl-2-[(S)-2,2,2-trifluoro-1-(4'-methanesulfonyl-biphenyl-4-yl)-ethylamino]-butyramide (S)—N—-[(S)-Cyano-(4-cyano-2,6-difluoro-benzyl)-methyl]-2-{(S)-1-[4'-((R)-2,2-difluoro-1-hydroxy-ethyl)-biphenyl-4-yl]-2,2,2-trifluoro-ethylamino}-3-methyl-butyramide (S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-3-ylmethyl)-methyl]-amide (S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-4-ylmethyl)-methyl]-amide (S)-4-Fluoro-4-methyl-2-[(S)-2,2,2-trifluoro-1-(4'-methanesulfonyl-biphenyl-4-yl)-ethylamino]-pentanoic acid [(S)-cyano-(2,6-difluoro-benzyl)-methyl]-amide or a pharmaceutically acceptable salt or stereoisomer thereof.

Also included within the scope of the present invention is a pharmaceutical composition which is comprised of a compound as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Exemplifying the invention is the use of any of the compounds described above in the preparation of a medicament for the treatment and prevention of one or more of toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis in a mammal in need thereof.

The compounds of this invention may be administered to mammals, preferably humans, either alone or preferably in combination with pharmaceutically acceptable carriers or diluents, optionally with known adjuvants, such as alum, in a pharmaceutical composition, according to standard pharmaceutical practice. The compounds can be administered by one or more of the following, orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, is commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing parasitic diseases, including toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis. Combinations of the presently disclosed compounds with other agents useful in treating or preventing parasitic diseases are within the scope of the invention. A person of ordinary skill in the art would be able to discern which combinations of agents would be useful based on the particular characteristics of the drugs and the disease involved.

Existing therapies for Chagas Disease include, but are not limited to nifurtimox, benznidazole, allopurinol. Drugs that may have an effect on the parasite include but are not limited to terbinafine, lovastatin, ketoconazole, itraconazole, posaconazole, miltefosine, ilmofosine, pamidronate, alendronate, and risedronate. Other mechanisms being explored for the treatment of Chagas Disease include, but are not limited to inhibitors of trypanothione reductase and inhibitors of hypoxanthine-guanine phosphoribosyl transferase (HGPRT), See, Urbina, Current Pharmaceutical Design, 8, 287-295, 2002)

Existing therapies for malaria include, but are not limited to chloroquine, proguanil, mefloquine, quinine, pyrimethamine-sulphadoxine, doxocycline, berberine, halofantrine, primaquine, atovaquone, pyrimethamine-dapsone, artemisinin and quinhaosu.

Existing therapies for leishmaniasis include, but are not limited to meglumine antimonite, sodium stibogluconate and amphotericin B.

Existing therapies for schistosomiasis include, but are not limited to praziquantel and oxamniquine.

Existing therapies for African trypanosomiasis include, but are not limited to pentamidine, melarsoprol, suramin and eflornithine.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein is an amount of active compound or pharmaceutical agent that is effective to prevent or slow the development of, or to partially or totally alleviate the existing symptoms in, a particular disease, condition or infection for which the subject is being treated (e.g., parasitic disease caused by parasites that rely on cruzipain or a similar cysteine protease for one or more life-cycle functions such as *T. cruzi*). Determination of a therapeutically effective amount is well within the capability of those skilled in the art.

The terms "treating" or "treatment" of a disease as used herein includes lessening, ameliorating, decreasing and/or inhibiting the disease, e.g., causing the clinical symptoms of the disease or the development of the disease to lessen, decrease, arrest or withdraw; or relieving the disease, e.g., causing regression of the disease or its clinical symptoms.

The terms "prevent" or "preventing" of a disease as used herein includes causing the clinical symptoms of the disease not to develop in a mammal that may be exposed to or predisposed to the disease or likely to get the disease (i.e., by travel to an affected geographical region or having a genetic predisposition) but does not yet experience or display symptoms of the disease; inhibiting the disease.

The terms "once weekly" and "once-weekly dosing", as used herein, means that a unit dosage, for example a unit dosage of a compound of the instant invention, is administered once a week, i.e., once during a seven-day period, preferably on the same day of each week. In the once-weekly dosing regimen, the unit dosage is generally administered about every seven days. A non-limiting example of a once-weekly dosing regimen would entail the administration of a unit dosage of the compound every Sunday. It is customarily recommended that a unit dosage for once-weekly administration is not administered on consecutive days, but the once-weekly dosing regimen can include a dosing regimen in which unit dosages are administered on two consecutive days falling within two different weekly periods.

The present invention also encompasses a pharmaceutical composition useful in the treatment of parasitic diseases caused by parasites that rely on cruzipain or a similar cysteine protease for one or more life-cycle functions (e.g., *T. cruzi*), comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a parasitic disease. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200, 250, 300, 400 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In another exemplary application, oral dosages of the present invention, when used for the indicated effects, will range between about 0.01 mg per kg of body weight per week (mg/kg/week) to about 10 mg/kg/week, preferably 0.1 to 10 mg/kg/week, and most preferably 0.1 to 5.0 mg/kg/week. For oral administration, the compositions are preferably provided in the form of tablets containing 2.5 mg, 3.5 mg, 5 mg, 10 mg, 20 mg, 25 mg, 35 mg, 40 mg, 50 mg, 80 mg, 100 mg, 200 mg, 400 mg, and 500 mg of the active ingredient for the symptomatic adjustment of the dosage to the patient to be treated. A medicament typically contains from about 2.5 mg to about 200 mg of the active ingredient, specifically, 2.5 mg, 3.5 mg, 5 mg, 10 mg, 20 mg, 25 mg, 35 mg, 40 mg, 50 mg, 80 mg, 100 mg, 200 mg, 400 mg and 500 mg of active ingredient. Alternatively, the compounds of the instant invention may be administered in a biweekly, twice monthly or monthly dose.

The compounds of the present invention can be used in combination with other agents useful for treating parasitic diseases. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly.

These and other aspects of the invention will be apparent from the teachings contained herein.

DEFINITIONS

The compounds of the present invention may have asymmetric centers, chiral axes, and chiral planes (as described in:

E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof

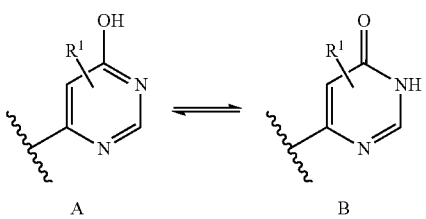

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms.

It is understood that when no reference is made to a particular stereoisomer, then the compound can be in either conformation. When reference to the conformation of one or more positions is specified, it is understood that conformation of the remaining unspecified positions can be in either orientation. When reference is made to a stereoisomer, it is understood that both the compound itself and its pharmaceutically acceptable salt are included.

As used herein, "alkyl" is intended to include both branched and straight-chain saturated aliphatic hydrocarbon groups having the no more than 10 carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on. In specific embodiments, the term alkyl refers to branched and straight-chain saturated aliphatic hydrocarbon groups having 1-6 carbon atoms. "Alkoxy" represents an alkyl group of indicated number of carbon atoms attached through an oxygen bridge.

As used herein, "alkene" is intended to include both branched and straight-chain saturated aliphatic hydrocarbon groups having 2-6 carbon atoms and at least one carbon to carbon double bond. For example, $C_2$-$C_6$, as in "$C_2$-$C_6$ alkene" is defined to include groups having 2, 3, 4, 5 or 6 carbons with at least one carbon to carbon double bond in a linear, branched or cyclic arrangement. For example, "$C_2$-$C_6$ alkene" specifically includes ethylene, propene, butene, pentene, hexene, and so on.

As appreciated by those of skill in the art, "halo" or "halogen" as used herein is intended to include chloro, fluoro, bromo and iodo.

The term "keto" means carbonyl (C=O).

The term "alkoxy" as used herein means an alkyl portion, where alkyl is one to six carbon atoms in a linear, branched, or cyclic arrangement, connected to the remainder of the molecule via an oxygen atom. Examples of alkoxy include methoxy, ethoxy and the like.

The term "haloalkyl" includes an alkyl portion, where alkyl is one to six carbon atoms in a linear, branched, or cyclic arrangement, which is substituted with one to five halo.

The term "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen atom, it is understood that the corresponding N-oxides thereof are also encompassed by this definition.

The term "aryl" is intended to mean any stable monocyclic or bicyclic carbon ring up to 12 atoms in each ring, wherein at least one ring is aromatic. Examples of such aryl elements include but not limited to phenyl, naphthyl, biphenyl or indanyl. In cases where the aryl substituents is bicyclic and one ring is non-aromatic, it is understood that attachment is via the aromatic ring. In a specific embodiment, the aryl is phenyl.

The term "heteroaryl", as used herein, represents a stable monocyclic, bicyclic or tricyclic ring up to 10 atoms in each ring, wherein at least one ring is aromatic and contains from 1-4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "arylalkyl" includes an alkyl portion where alkyl is one to six carbon atoms in a linear, branched, or cyclic arrangement and includes an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluoyl, ethylphenyl, and propylphenyl.

The term "heteroarylalkyl" as used herein, shall refer to a system that includes a heteroaryl portion, where heteroaryl is as defined above, and contains an alkyl portion of one to six carbon atoms in a linear, branched, or cyclic arrangement. Examples of heteroarylalkyl include, but are not limited to, thienylmethyl, thienylethyl, thienylpropyl, pyridylmethyl, pyridylethyl and imidazoylmethyl.

The term "haloalkoxy" represents a radical —OR where R is alkyl having one to six carbon atoms in a linear, branched, or cyclic arrangement that is substituted with one to five, preferably one to three, halogens. Representative examples include, but are not limited to trifluoromethyloxy, dichloroethyloxy, and the like.

The term "hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to hydroxymethyl, 2-hydroxyethyl, 2-hydroxypropyl, 3-hydroxypropyl, and the like.

The term "halo hydroxyalkyl" means a linear monovalent hydrocarbon radical of one to six carbon atoms or a branched monovalent hydrocarbon radical of three to six carbons substituted with one or two hydroxy groups and with 1, 2 or 3 halo. Representative examples include, but are not limited to 2,2,2-trifluoro-1-hydroxyethyl, 2,2-difluoro-1-hydroxyethyl and the like.

The term "cycloalkyl" or "carbocycle" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl and heterocyclyl substituents may be unsubstituted or unsubstituted, unless specifically defined otherwise.

For example, a $(C_1-C_6)$alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C=O)CH$_2$CH(OH)CH$_3$, —(C=O)OH, —CH$_2$(OH)CH$_2$CH(O), and so on.

Whenever the term "alkyl" or its prefix root appears in a name of a substituent (e.g., aryl $C_{0-8}$ alkyl) it shall be interpreted as including those limitations given above for "alkyl." Designated numbers of carbon atoms (e.g., $C_{1-6}$) shall refer independently to the number of carbon atoms in an alkyl or cyclic alkyl moiety or to the alkyl portion of a larger substituent in which alkyl appears as its prefix root.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:
AcOH=acetic acid
BaSO$_4$=barium sulfate
BOC=t-butyloxycarbonyl
CBr$_4$=carbon tetrabromide
CCl$_4$=carbon tetrachloride
CH$_2$Cl$_2$=methylene chloride
DCC=dicyclohexylcarbodiimide
DCM=dichloromethane
DME=dimethyl ether
DMF=N,N-dimethylformamide
DMSO=dimethylsulfoxide
DPPF=1,1'-bis(diphenylphosphino)ferrocene
Et$_3$N=triethylamine
EtOH=ethanol
HATU=o-(7-azabenzotriazol-1-yl)-N,N,N',N'-tetramethyl-uronium hexafluorophosphate
HBTU=o-Benzotriazole-N,N,N',N'-tetramethyl-uronium-hexafluoro-phosphate
HBr=hydrogen bromide
HCl=hydrogen chloride
K$_2$CO$_3$=potassium carbonate
MeCN=acetonitrile
MeOH=methanol
MeSO$_3$H=methane sulfonic acid
Mg SO$_4$=magnesium sulfate
NaBH$_4$=sodium borohydride
NaOH=sodium hydroxide
Na$_2$SO$_4$=sodium sulfate
NBS=N-bromosuccinimide
NH$_4$OH=ammonium hydroxide
PCl$_5$=phosphorous pentachloride
PdCl$_2$(dppf)=[1,1'-bis(diphenylphosphino)ferrocene]dichloropalladium(II)
Pd$_2$(dba)$_3$=tris(dibenzylideneacetone)dipalladium(0)
PG=protecting group
PPh$_3$=triphenylphosphine
PyBOP=benzotriazol-1-yloxytris(pyrrolidino)phosphonium-hexafluorophosphate
rt=room temperature
sat. aq.=saturated aqueous
SOCl$_2$=thionyl chloride
TFAA=trifluoroacetic acid
THF=tetrahydrofuran
ZnCN$_2$=zinc cyanide
ZN(BH$_4$)$_2$=zinc borohydride
tlc=thin layer chromatography
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl The compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEMES

Compounds of the present invention can be prepared according to Scheme 1, as indicated below. Thus the methyl group of a substituted toluene can be brominated under radicalar reaction conditions. Alternatively, a benzilic alcohol can be brominated by using reagent such as PPh$_3$ and CBr$_4$ to afford benzilic bromide. The resulting benzylic bromide can be used to alkylate N-(diphenylmethylene)amino acetonitrile. The imine can be then hydrolyzed using an acid such as AcOH. The free amine can be coupled to a carboxylic acid using different coupling agents such as PyBOP, HBTU or HATU. The final material can be resolved by chiral HPLC on a chiral column such as chiralpak A/D.

SCHEME 1
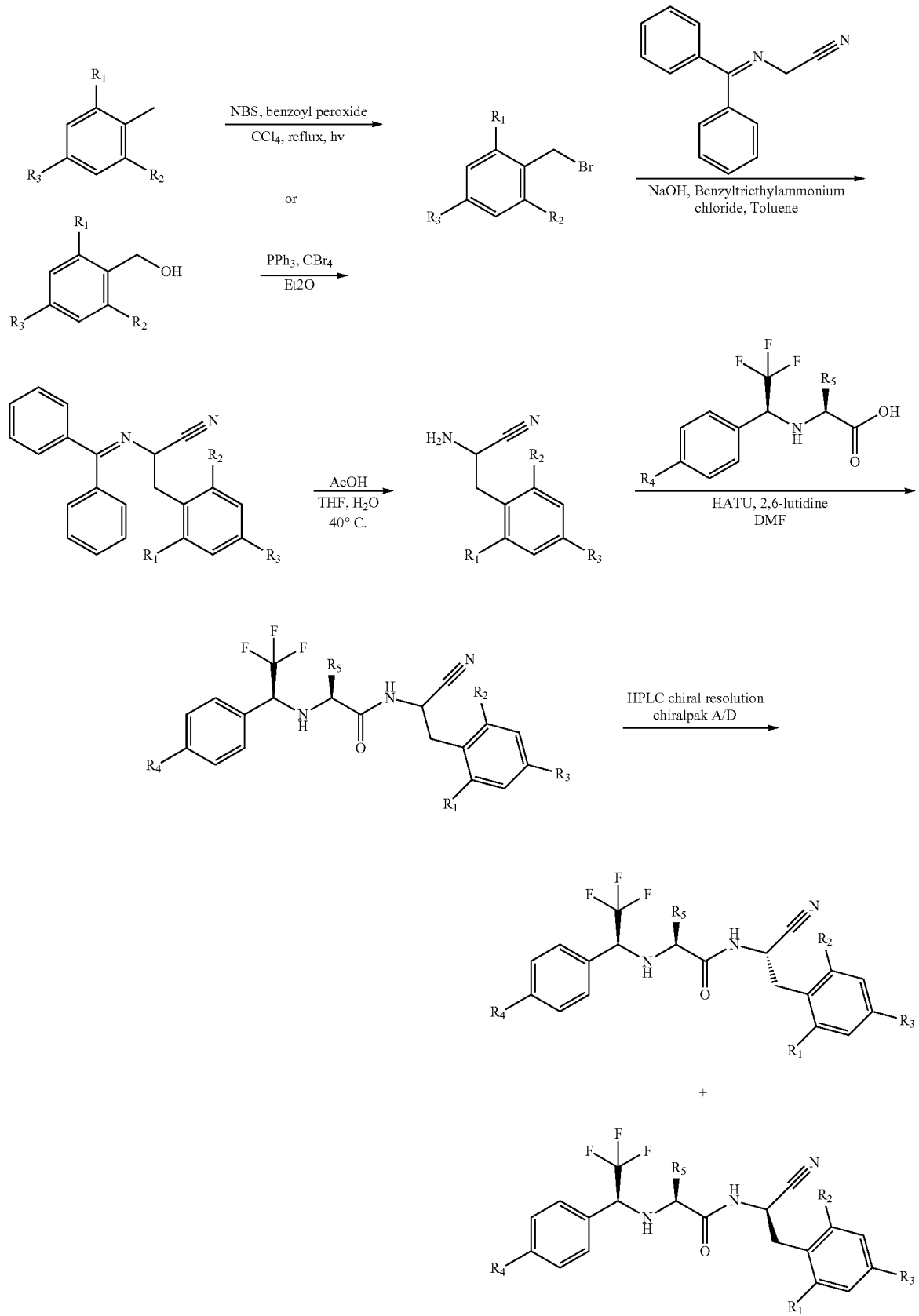

R1, R2 = H, F or Cl
R3 = H, Cl, CN, F, CF3, Br or I
R4 = Ar or Br

R5 = 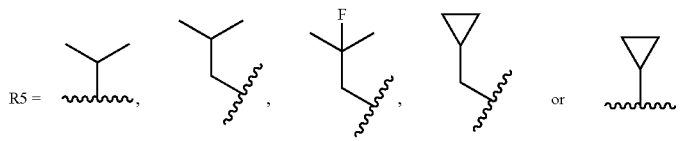

Compounds of the present invention may also be prepared according to Scheme 1A, as indicated below. The α-aminonitrile obtained in Scheme 1 can be directly resolved by chiral HPLC using a chiral column such as chiralpak A/D. Like in Scheme 1, the free amine can be coupled to a carboxylic acid using different coupling agents such as PyBOP, HBTU or HATU. This peptidic coupling will provide a single enantiomer of the same compounds as described in Scheme 1.

SCHEME 1A

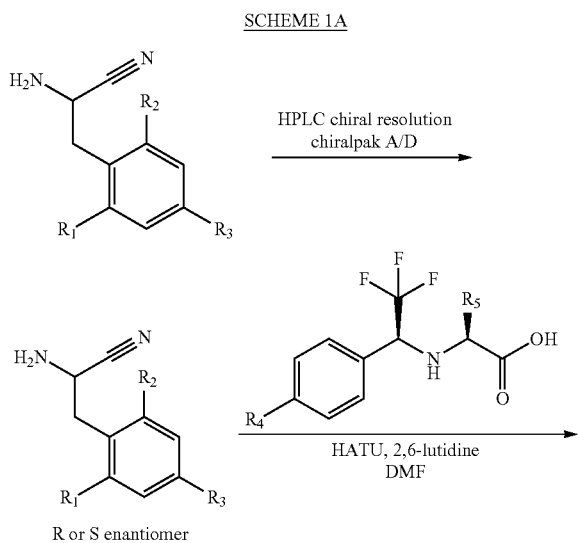

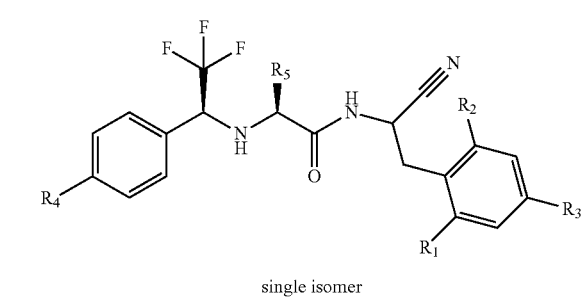

single isomer

R1, R2 = H, F or Cl
R3 = H, Cl, CN, F, CF3, Br or I
R4 = Ar or Br

Compounds of the present invention may also be prepared according to Scheme 1B, as indicated below. When the phenyl ring of the left end of the compound described in scheme 1 is substituted by a halogen atom such as bromide atom, the former compound could be further functionalized with aryl group using Suzuki coupling conditions.

SCHEME 1B

When R4 = Br

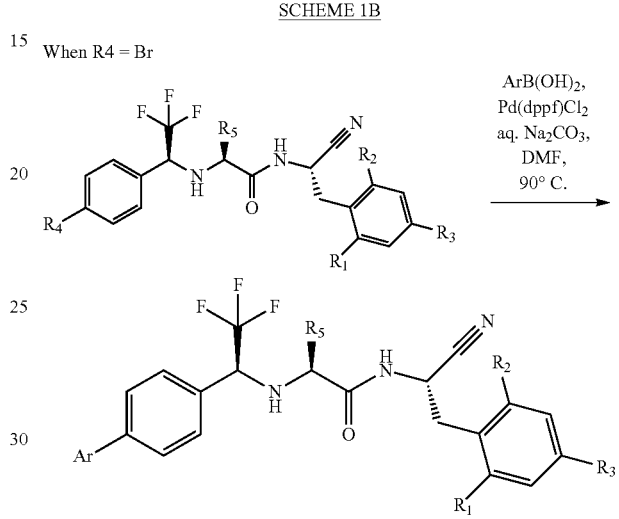

Compounds of the present invention may also be prepared according to Scheme 1C, as indicated below. When the phenyl ring of the right end of the compound described in scheme 1 is substituted by a halogen atom such as bromide atom, the former compound could be further functionalized with aryl group using Suzuki coupling conditions. Cyano group could also be introduced by using palladium coupling conditions as well as methylsulfone which could be introduced by copper mediated reaction.

SCHEME 1C

When R3 = Br or I

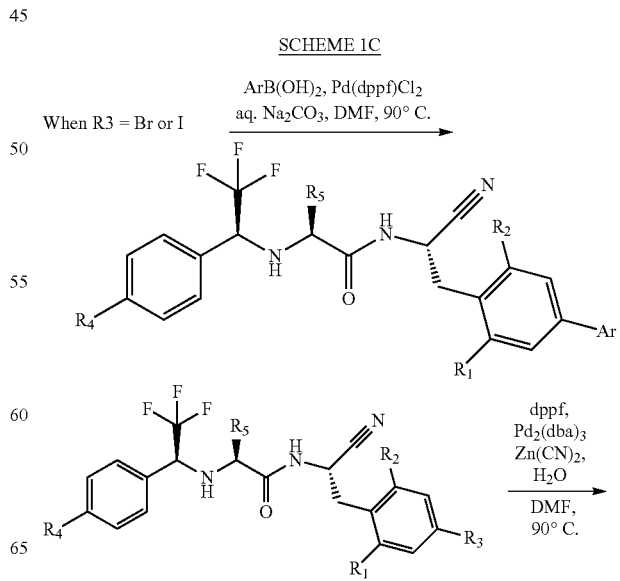

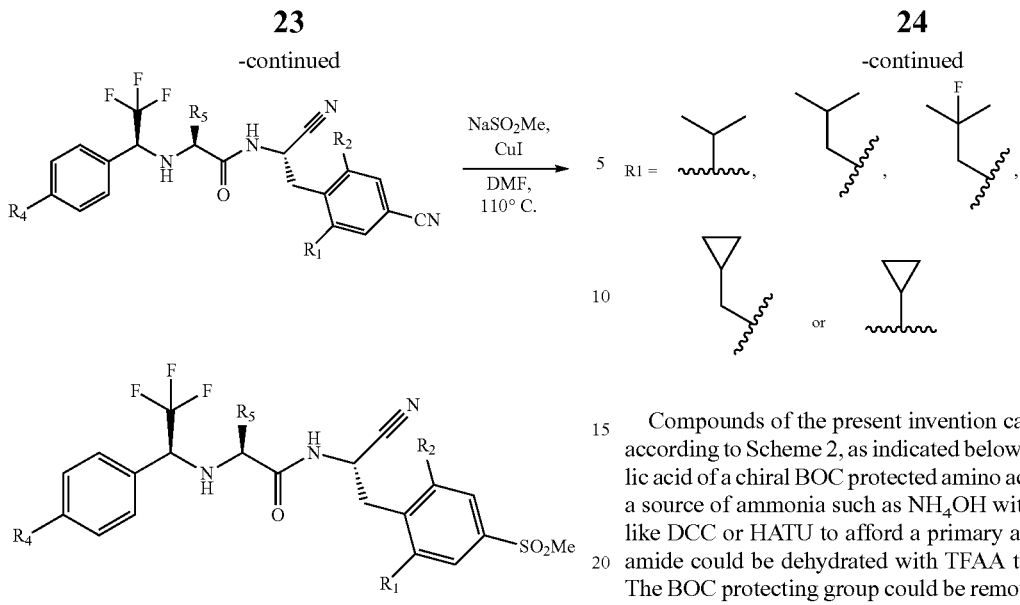

Carboxylic acids used in scheme 1 and scheme 1A to afford compounds of the present invention may be prepared according to Scheme 1D, as indicated below. The ester of natural or unnatural amino acid was reacted with a carbonyl group like a trifluoroketone to form an imine which is further reduced with a reducing agent like NaBH$_4$ or Zn(BH$_4$)$_2$. The resulting carboxylic acid can be directly coupled to an amine as in scheme 1 and scheme 1A or optionally further functionalized by coupling reaction such as Suzuki coupling type reaction Compounds of the present invention can also be prepared according to Scheme 2, as indicated below. Thus the carboxylic acid of a chiral BOC protected amino acid could react with a source of ammonia such as NH$_4$OH with a coupling agent like DCC or HATU to afford a primary amide. The primary amide could be dehydrated with TFAA to provide a nitrile. The BOC protecting group could be removed in the presence of a strong acid such as TFA or MeSO$_3$H. The free amine can be coupled to a carboxylic acid using different coupling agents such as PyBOP, HBTU or HATU to afford the desired material. This material could be further reacted under Suzuki type coupling reaction to afford further functionalized compounds.

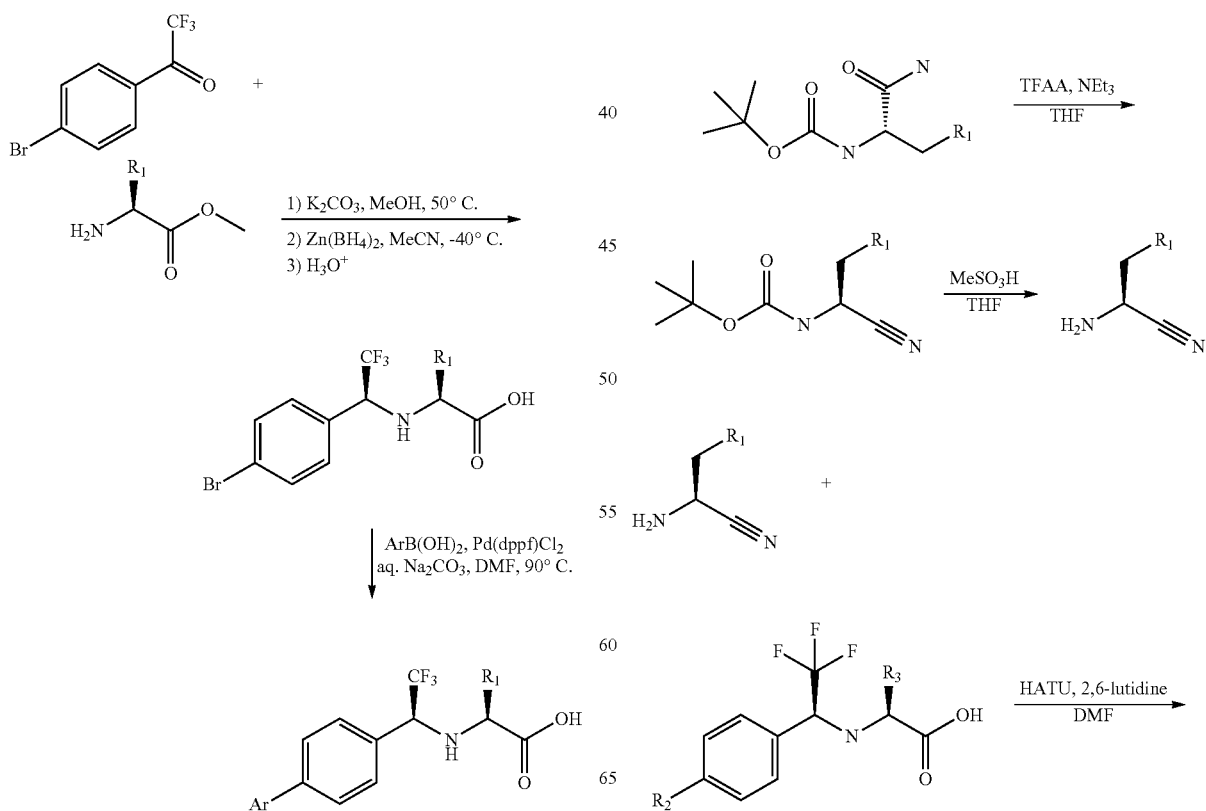

-continued

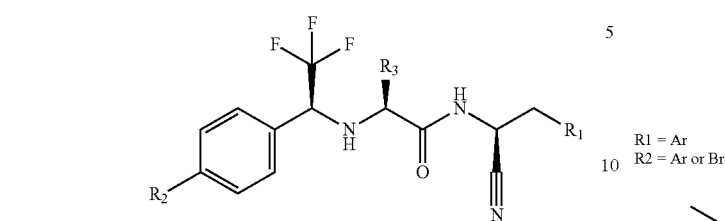

When R2 = Br

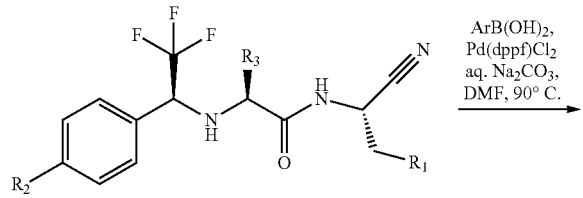

ArB(OH)₂,
Pd(dppf)Cl₂
aq. Na₂CO₃,
DMF, 90° C.

-continued

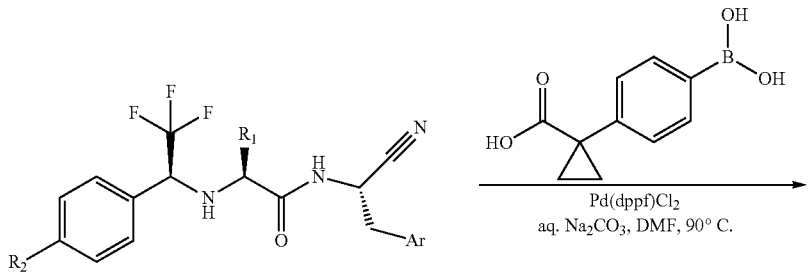

R1 = Ar
R2 = Ar or Br

R3 = (isopropyl), (isobutyl), (fluoro-tert-butyl-like), (cyclopropyl), or (cyclopropylmethyl)

Compounds of the present invention can also be prepared according to Scheme 3, as indicated below. Thus, cyclopropanecarboxylic acid intermediate can be prepared from Suzuki coupling type reaction with appropriate boronic acid or ester. Amides can then be prepared from the coupling of amines with the acid by using a coupling agent like DCC or HATU.

SCHEME 3

When R2 = Br

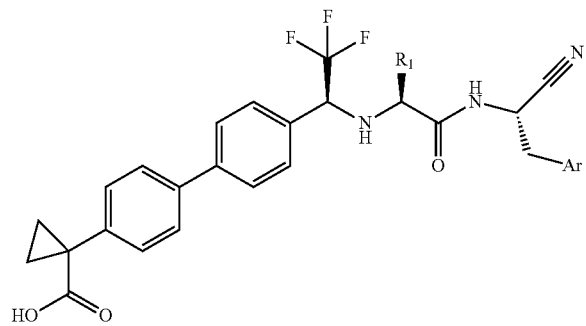

Pd(dppf)Cl₂
aq. Na₂CO₃, DMF, 90° C.

HATU, 2,6-lutidine
NR₂R₃
DMF

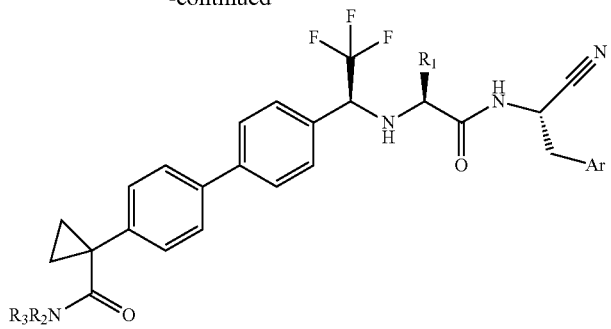

Compounds of the present invention may be prepared according to Scheme 4, as indicated below. The L-aspartic acid was reacted with hexafluoroacetone to provide the free β-carboxylic acid. This acid was turned into an acid chloride in the presence of a source of chlorine such as thionyl chloride. The acid chloride was reduced to the aldehyde in the presence of a palladium catalyst and hydrogen. The aldehyde was reacted with $PCl_5$ in chlorinated solvents to provide the gem-dichloro alkyl. The protecting group was cleaved in the presence of a strong acid like HBr to free the newly formed amino acid. The carboxylic acid was esterified in an alcoholic solvent such as ethanol in the presence of acetyl chloride. The amino ester was reacted with a carbonyl group like a ketone or an aldehyde to form an imine which is further reduced with a reducing agent like $NaBH_4$ or $Zn(BH_4)_2$. The carboxylic acid can be coupled to the free amine formed in Scheme 1 or 2 using different coupling agents such as PyBOP, HBTU or HATU. Then, a Suzuki coupling provided the compound of the invention.

SCHEME 4

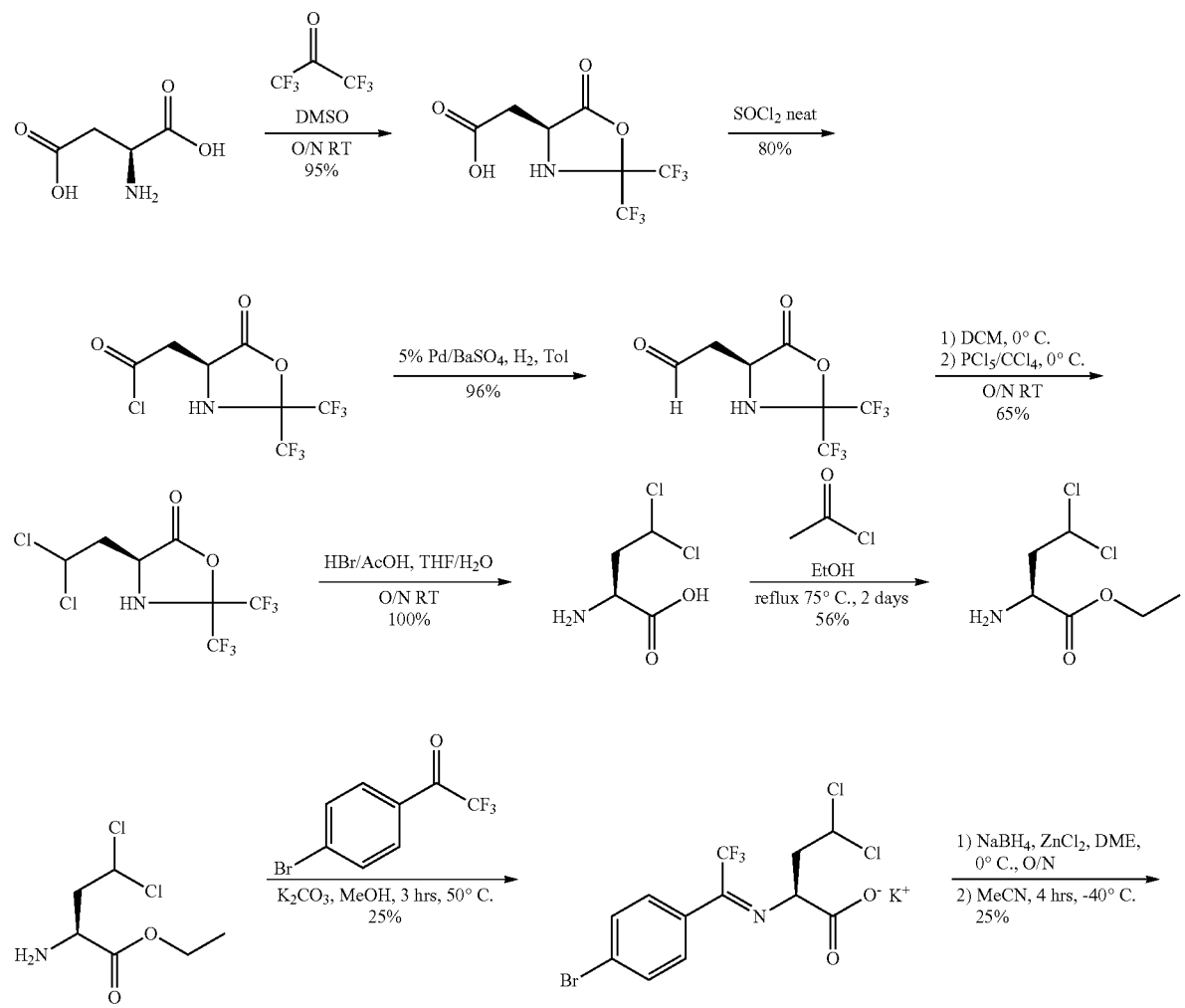

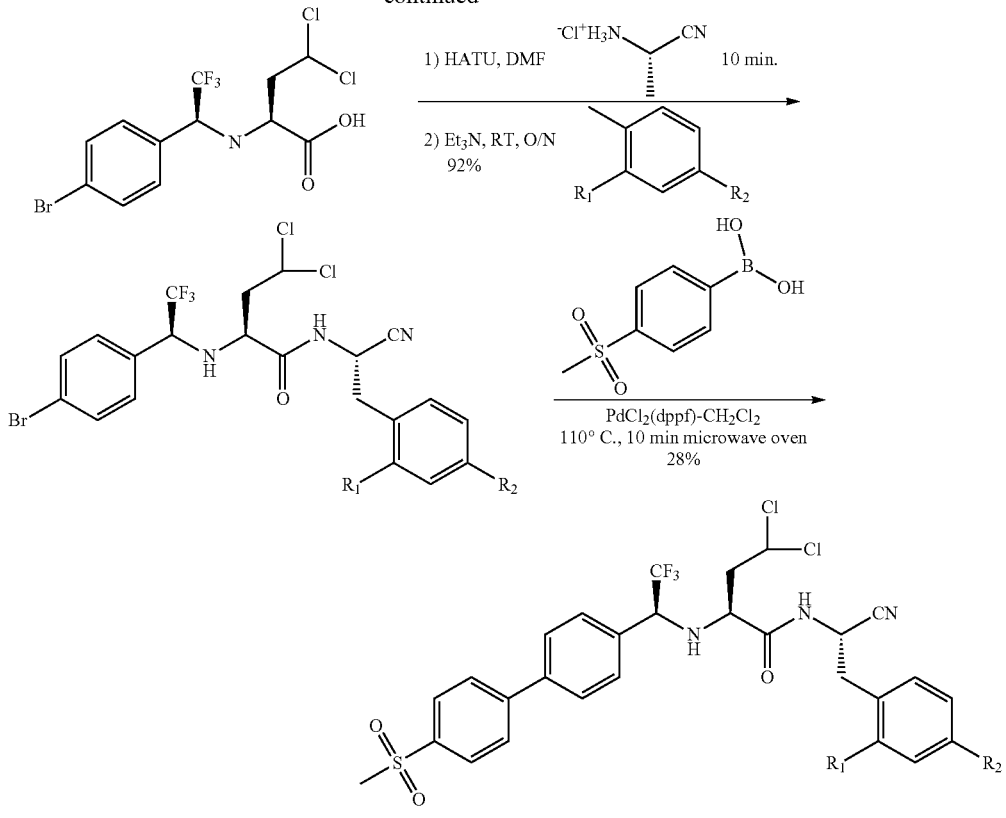

R1 = H or F
R2 = H or CN

Example 1

Synthesis of (S)-4,4-Dichloro-N—-[S)-cyano-(4-cyano-2-fluoro-benzyl)-methyl]-2-[(S)-2,2,2-trifluoro-1-(4'-methanesulfonyl-biphenyl-4-yl)-ethylamino]-butyramide

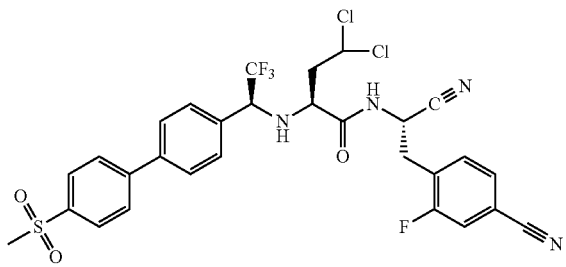 [SMILES: CS(=O)(=O)c1ccc(-c2ccc([C@H](N[C@@H](CC(Cl)Cl)C(=O)N[C@H](C#N)Cc3ccc(C#N)cc3F)C(F)(F)F)cc2)cc1]

Step 1: Preparation of [(4S)-5-oxo-2,2-bis(trifluoromethyl)-1,3-oxazolidin-4-yl]acetic acid To a room temperature DMSO (60 ml) solution of L-aspartic acid (20 g) in a 250 ml three necked round bottom flask equipped with a dry ice condenser (cold finger) and inlet bubbler was bubbled hexafluoroacetone for 1 h. Foaming occurred preventing the stir bar from spinning. The reaction was stirred for 1 hr. More gas was bubbled into the now cloudy solution (no longer foamy). The solution was stirred for 30 minutes. Gas was bubbled into the solution. The solution was left overnight allowing the dry ice to melt until it reached room temperature with spinning. The solution was mostly clear in the morning with only few solid particles. The solution was poured onto 300 ml of water and 150 ml DCM. The whole mixture was filtered through celite to facilitate separation. When shaken the clear solution became white. Separation was slow, therefore added 500 ml of DCM and water. The solution became clear. The combined organic layers were back washed twice with water to remove any trace DMSO. The organic layer was then dried with $Na_2SO_4$, filtered, and concentrated under reduced pressure to yield the title compound, a residue which was used as such in the next reaction.

$^1$H NMR δ (ppm) ($CDCl_3$): 4.36 (1H, dd, J=9.68, 2.79 Hz), 3.01 (1H, dd, J=17.59, 2.88 Hz), 2.73 (1H, dd, J=19.04, 9.44 Hz).

Step 2: Preparation of [(4S)-oxo-2,2-bis trifluoromethyl)-1,3-oxazolidin-4-yl]acetyl chloride $SOCl_2$ (56 ml) was slowly added to the acid (22 g). The resulting mixture was stirred for 2 hours. The solution was then heated in an oil bath at 70° C. overnight. The reaction was allowed to cool down. Thionyl chloride was evaporated. The yellow-orange oil was purified by distillation. It was collected between 70° C. and 92° C.

$^1$H NMR δ (ppm)($CDCl_3$): 4.43 (1H, ddd, J=9.93, 6.98, 2.40 Hz), 3.59-3.52 (2H, m), 3.24 (1 to H, dd, J=18.60, 9.82 Hz).

Step 3: Preparation of [(4S)-5-oxo-2,2-bis(trifluoromethyl)-1,3-oxazolidin-4-yl]acetaldehyde The acid chloride (25 g) was dissolved in toluene (278 ml) and the unreduced 5% Pd/BaSO$_4$ (20 g) was added. It was submitted to hydrogenation in a Parr reactor (40 psi) for 24 h. The reaction mixture was filtered on a pad of celite. The filtrate was concentrated and the aldehyde was used without further purification.

$^1$H NMR δ (ppm)(CDCl$_3$): 9.82 (1H, s), 4.43 (1H, t, J=8.44 Hz), 3.53 (1H, s), 3.21 (1H, dd, J=19.13, 2.28 Hz), 2.89 (1H, dd, J=19.11, 10.06 Hz).

Step 4: Preparation of (4S)-4-(2,2-dichloroethyl)-2,2-bis(trifluoromethyl)-1,3-oxazolidin-5-one The aldehyde was dissolved in dichloromethane and it was stirred under N$_2$ gas in an ice bath. PCl$_5$ was dissolved in CCl$_4$ and stirred in an ice bath. After 30 minutes the PCl$_5$ solution was added to the first one. It was stirred at room temperature overnight. The clear solution was added onto saturated aqueous NaHCO$_3$. The aqueous layer was extracted with diethyl ether. The organic layer was washed with brine and dried over MgSO$_4$. Crude product was purified by flash chromatography (5:95 to 10:90 EtOAc/hexanes).

$^1$H NMR δ (ppm)(CDCl$_3$): 5.97 (1H, t, J=6.16 Hz), 4.36-4.30 (1H, m), 3.37 (1H, d, J=7.15 Hz), 2.79-2.73 (1H, m), 2.56-2.50 (1H, m).

Step 5: Preparation of (2S)-2-amino-4,4-dichlorobutanoic acid

The protected amino acid (14.8 g) was dissolved in THF (100 ml) and water (100 ml). 45% HBr/AcOH (8 ml) solution was added. The solution was stirred at room temperature for 12 h. The progress of the reaction was followed by NMR. 2 extra ml of HBr in acetic acid were added after 12 hours, 4 extra ml of HBr in acetic acid were added after 24 hours and 3 extra ml of HBr in acetic acid were added after 48 hours. N$_2$ was bubbled into the solution for 30 min prior to evaporation of the solvents. The mixture was concentrated under reduced pressure and was co-evaporated three times with toluene. The amino acid was used without further purification.

$^1$H NMR δ (ppm) (DMSO-d$_6$): 8.37 (3H, s), 6.34 (1H, t, J=6.63 Hz), 4.01 (1H, d, J=7.08 Hz), 2.79-2.61 (2H, m).

Step 6: Preparation of ethyl (2S)-2-amino-4,4-dichlorobutanoate

Acetyl chloride (18.7 ml) was added drop wise to ethanol (185 ml). This solution was added to the amino acid (7.5 g). The mixture was refluxed overnight (75° C.). The mixture was concentrated under reduced pressure and used without further purification.

$^1$H NMR δ (ppm) (DMSO-d$_6$): 8.68 (3H, s), 6.47 (1H, t, J=6.60 Hz), 4.23 (2H, q, J=7.12 Hz), 2.80-2.72 (2H, m), 1.26 (3H, t, J=7.10 Hz).

Step 7: Preparation of (2S)-2-{[(1S)-1-(4-bromophenyl)-2,2,2-trifluoroethyl]amino}-4,4-dichlorobutanoic acid The amino ester (4.6 g) and potassium carbonate (7.9 g) were mixed in anhydrous methanol (13.5 ml). 1-(4-bromophenyl)-2,2,2-trifluoroethanone (5.8 g) was added and the mixture was heated to 50° C. for 8 hours. The mixture was filtered over a pad of celite and the filtrate was concentrated. The resulting imine was used as such. A Zn(BH$_4$)$_2$ solution was prepared by adding 790 mg of NaBH$_4$ to a 0° C. suspension of 1.4 g of ZnCl$_2$ in 10.5 ml of DME. The mixture was stirred overnight. From this mixture 4 ml was transferred to another round bottom flask. The imine was diluted in MeCN (67.4 ml) and added to the Zn(BH$_4$)$_2$ suspension which had been cooled at −40° C. The mixture was stirred at −40° C. for 4 h. The reaction was quenched with 10 ml of acetone and allowed to warm to room temperature for 1 h. 1M aqueous HCl (50 ml) was added slowly. The solution was concentrated under reduced pressure and the mixture was extracted with EtOAc. Organic layer was washed with brine and dried over MgSO$_4$, filtered and concentrated. Crude material was purified by flash (20:80 EtOAc/hexanes to 100% EtOAc) to afford the carboxylic acid.

$^1$H NMR δ (ppm)(CH$_3$OH-d$_4$): 7.61-7.53 (2H, m), 7.41-7.35 (2H, m), 6.19 (1H, dd, J=9.06, 4.09 Hz), 4.31 (1H, d, J=7.50 Hz), 3.64 (1H, dd, J=9.87, 4.25 Hz), 2.56 (1H, dd, J=9.30, 4.41 Hz), 2.47 (1H, dd, J=10.03, 4.19 Hz).

Step 8: Preparation of (2S)-2-{[(1S)-1-(4-bromophenyl)-2,2,2-trifluoroethyl]amino}-4,4-dichloro-N-[(1S)-1-cyano-2-(4-cyano-2-fluorophenyl)ethyl]butanamide (2S)-2-{[(1S)-1-(4-bromophenyl)-2,2,2-trifluoroethyl]amino}-4,4-dichlorobutanoic acid (120 mg) and (1S)-1-cyano-2-(4-cyano-2-fluorophenyl)ethanaminium chloride (66 mg) were dissolved in DMF (1.5 ml) and HATU (223 mg) was added. The reaction mixture was stirred at room temperature for 5 min and Hunig's base (204 µL) was added. The solution was stirred for 18 hours. The mixture was poured onto an aqueous sodium hydrogen carbonate (saturated, 20 ml) and water (20 ml). The mixture was stirred in an erlenmeyer flask for 10 min. The aqueous layer was extracted with EtOAc. The organic layer was washed with brine, dried on MgSO4. It was concentrated under reduced pressure. The crude product was purified by flash (eluted with 20:80 to 55:45 EtOAc/hexanes).

$^1$H NMR δ (ppm)(CDCl$_3$): 7.59-7.52 (3H, m), 7.50-7.42 (2H, m), 7.26-7.20 (2H, m), 5.98 (1H, t, J=6.36 Hz), 5.13-5.06 (1H, m), 4.18-4.07 (1H, m), 3.43 (1H, q, J=7.42 Hz), 3.26 (1H, dd, J=13.92, 7.03 Hz), 3.16 (1H, dd, J=13.97, 7.20 Hz), 2.56-2.38 (2H, m), 2.38-2.36 (1H, m).

Step 9: Preparation of (2S)-4,4-dichloro-N-[(1S)-1-cyano-2-(4-cyano-2-flurophenyl)ethyl]-2-({(1S)-2,2,2-trifluoro-1-[4'-(methylsulfonyl)biphenyl-4-yl]ethyl}amino)butanamide In a microwave tube, (2S)-2-{[(1S)-1-(4-bromophenyl)-2,2,2-trifluoroethyl]amino}-4,4-dichloro-N-[(1S)-1-cyano-2-(4-cyano-2-fluorophenyl)ethyl]butanamide, [4-(methylsulfonyl)phenyl]boronic acid, and Na$_2$CO$_3$ (2M) were dissolved in DMF (1.35 ml) and degassed with N$_2$. PdCl$_2$(dppf)-CH$_2$Cl$_2$ adduct was added. The tube was sealed and heated in a microwave at 110° C. for 600 seconds. The reaction mixture was worked up with aqueous sodium hydrogen carbonate (saturated, 50 ml) was added and the mixture was extracted with ethyl acetate (3×50 ml). The combined organic fractions were washed with brine (2×50 ml), dried over MgSO$_4$, filtered and the solvent was evaporated under reduced pressure. The crude product was purified by flash chromatography (27:63 to 55:45 EtOAc/hexanes).

M+1, +ESI=655

Example 2

Synthesis of (2S)—N-[(1S)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide

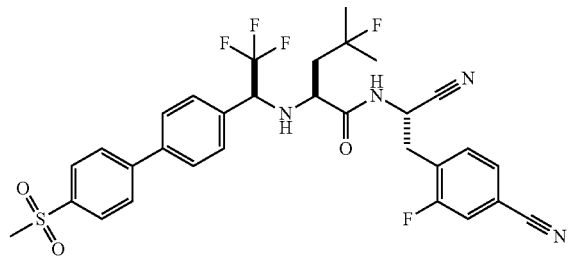 [SMILES: CC(C)(F)C[C@H](N[C@@H](c1ccc(-c2ccc(S(C)(=O)=O)cc2)cc1)C(F)(F)F)C(=O)N[C@H](C#N)Cc1ccc(C#N)cc1F]

Step 1: Preparation of 4-(bromomethyl)-3-fluorobenzonitrile

A mixture of 3-fluoro-4-methylbenzonitrile (29.54 g) and NBS (46.7 g) as a suspension in 1,2-dichloroethane (500 ml) was treated with benzoyl peroxide (4.24 g) in a flask mounted with a reflux condenser open to air. The flask was immersed in an oil bath at 75° C. and light shun on it with a sunlamp. A more vigorous reflux was suddenly observed and the reaction became homogeneous. The reaction was let stir at this temperature for a total of 2 hours then let cool to room temperature. Hexanes (500 ml) was added and the precipitate filtered and discarded. The filtrate was concentrated under reduced pressure to approximately 100 ml and taken up in ethyl acetate (200 ml). The reaction was washed with half saturated sodium bicarbonate (100 ml), then brine (100 ml). The organic layer was separated and dried over magnesium sulfate. The organic phase was concentrated under reduced pressure to give the benzylic bromide as a yellow solid that was used as such in the next step.

Step 2: Preparation of 4 {2-cyano-2-[(diphenylmethylene)amino]ethyl}-3-Fluorobenzonitrile To a suspension of sodium hydride (2.62 g) in dimethylformamide (100 ml) at 0° C. was slowly added a solution of [(diphenylmethylidene)amino]acetonitrile (13.20 g) in 40 ml of dimethylformamide. The reaction temperature varied between 2 and 8° C. during the addition. The color went from yellow to brown with gas evolution. The reaction mixture was stirred at 0° C. for 10 more minutes then 4-(bromomethyl)-3-fluorobenzonitrile from step 1 (12.72 g) was added very quickly in 60 ml of dimethylformamide. The temperature rose to 27° C. and the cold bath was removed. The reaction was stirred for 4 h. The flask content was poured into sodium dihydrogen phosphate solution (300 ml) and icy water (1.4 L). The mixture turned yellow and a big lump formed along with very small amounts of fine powder. The fine solid was filtered and the lump kept in the Erlenmeyer. The lump was dissolved in ether (500 ml) and put in a separating funnel along with water (200 ml). The phases were separated and the organic layer was washed with brine (100 ml) and dried over magnesium sulfate. The organic phase is concentrated under reduced pressure to give 4-{2-cyano-2-[(diphenylmethylene)amino]ethyl}-3-fluorobenzonitrile an orange solid that was used as such in the next step.

Step 3: Preparation of 4-[(2S)-(2-amino-2-cyanoethyl)]-3-fluorobenzonitrile

A solution of 4-{2-cyano-2-[(diphenylmethylene)amino]ethyl}-3-fluorobenzonitrile from step 2 (24.5 g) in tetrahydrofuran (190 ml) is treated with water (45 ml) then with acetic acid (90 ml) and let stir for 24 h at 40° C. Approximately 75% of the volatiles were then removed under reduced pressure. The residual solution is diluted with water (100 ml) and 1 N hydrochloric acid (25 ml), extracted with 2 portions (100 ml each) of diethyl ether then was made basic with 8N potassium hydroxide and aqueous potassium phosphate until pH 9-10 was reached. The aminonitrile was extracted with three portions (300 ml each) of ethyl acetate. The pooled organic layers were washed with brine, dried over sodium sulfate and concentrated under reduced pressure. The orange product gum was dissolved in ethanol (20 ml) and diluted with hexanes (20 ml). Aliquots of 500 mg were injected on chiralcel AD column using 50% ethanol:50% hexanes isocratic conditions. The faster nitrile is the wrong enantiomer (Rt=19 min) while after evaporation and coupling (step 4) the slower enantiomer (t=24 min) will lead to the potent diastereomer of the (2S)—N-[(1S)-1-cyano-2-(4-cyano-2-fluorophenyl)ethyl]-4-fluoro-4-methyl-2-({1(S)-2,2,2-trifluoro-1-[4'-(methylsulfonyl)biphenyl-4-yl]ethyl}amino) pentanamide that is assumed to be of S configuration.

Step 4: Preparation of (2S)—N-[(1S)-1-cyano-2-(4-cyano-2-fluorophenyl)ethyl]-4-fluoro-4-methyl-2-({1(S)-2,2,2-trifluoro-1-[4'-(methylsulfonyl)biphenyl-4-yl]ethyl}amino) pentanamide To (2S)-4-fluoro-4-methyl-2-({(1S)-2,2,2-trifluoro-1-[4'-(methylsulfonyl)biphenyl-4-yl]ethyl}amino) pentanoic acid dicyclohexylamine salt (301 mg) described in U.S. Pat. No. 7,183,425 (incorporated by reference in its entirety)., in dimethylformamide (5 ml) was added HATU (213 mg) and the solution was stirred for 1 minute. The slower amino nitrile (from step 3) (88 mg) and 2,6-lutidine (0.136 ml) are introduced at the same time and the reaction is stirred overnight. 1N HCl is added to the reaction media and the aqueous layer is extracted with EtOAc. The combined organic layers were washed with brine and water, dried over $Na_2SO_4$, filtered and concentrated. The crude compound was purified by automated $SiO_2$ flash chromatography system using solvent gradient of 10% EtOAc/Hex to 100% EtOAc/Hex to afford (2S)—N—-[(1S)-1-cyano-2-(4-cyano-2-fluorophenyl)ethyl]-4-fluoro-4-methyl-24 {1(S)-2,2,2-trifluoro-1-[4'-(methylsulfonyl)biphenyl-4-yl]ethyl}amino) pentanamide as a white solid. Slower amino nitrile gives more potent diastereomer (diagnostic in $^1$H NMR signal at 4.25 ppm for the active and 4.45 ppm for the inactive in d6-acetone).

M+1 (+ESI)=633.2

Example 3

Synthesis of (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-cyanophenyl)-ethyl]-amide

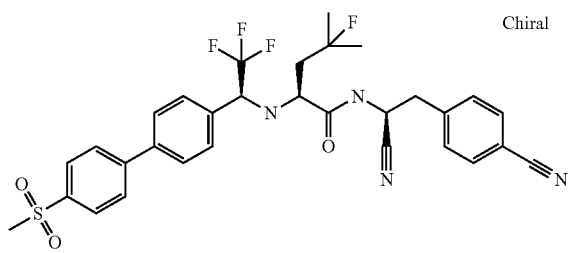 [SMILES: CC(C)(F)C[C@H](N[C@@H](c1ccc(-c2ccc(S(C)(=O)=O)cc2)cc1)C(F)(F)F)C(=O)N[C@H](C#N)Cc1ccc(C#N)cc1]

Step 1: Preparation of Nα-(tert-butoxycarbonyl)-4-iodo-L-phenylalaninamide

To (2S)-2-[(tert-butoxycarbonyl)amino]-3-(4-iodophenyl)propanoic acid in DMF (0.15M) at 0° C. was added HATU. 30% aqueous solution of NH$_4$OH was then slowly added and the reaction mixture was then stirred at 0° C. for 2 h. The mixture was poured into a saturated aqueous solution of sodium hydrogen bicarbonate and the aqueous layer was extracted with EtOAc. The combined organic layers were washed with brine and water, dried over Na$_2$SO$_4$, filtered and concentrated to yield desired amide.

Step 2: Preparation of tert-butyl [(1S)-1-cyano-2-(4-iodophenyl)ethyl]carbamate To Nα-(tert-butoxycarbonyl)-4-iodo-L-phenylalaninamide in THF (0.13 M) at 0° C. was added triethylamine. Trifluoroacetic anhydride) was then slowly added and the mixture was stirred for 2 h. Saturated aqueous solution of sodium hydrogen bicarbonate was added and the aqueous layer was extracted with EtOAc. The combined organic layers were washed with brine and water, dried over Na$_2$SO$_4$, filtered and concentrated. The crude compound was purified by automated SiO$_2$ flash chromatography system using solvent gradient of 5% EtOAc/Hex to 50% EtOAc/Hex to afford desired amino nitrile.

Step 3: Preparation of (1S)-1-cyano-2-(4-iodophenyl)ethanaminium chloride

To tert-butyl [(1S)-1-cyano-2-(4-iodophenyl)ethyl]carbamate in THF (0.4M) at rt is added methanesulfonic acid (10 eq). The mixture is stirred for 3 h and is poured into a saturated aqueous solution of sodium hydrogenbicarbonate, K$_3$PO$_4$ is added to bring pH of the mixture to pH ~9. The aqueous layer was extracted with EtOAc. The combined organic layers were washed with brine and water, dried over Na$_2$SO$_4$, filtered and concentrated. The crude compound was purified by automated SiO$_2$ flash chromatography system using solvent gradient of 50% EtOAc/Hex to 100% EtOAc/Hex. The free amine was dissolved in Et2O (0.3M) and treated with an excess of 2M HCl in diethyl ether. The mixture was stirred for 30 min. The resulting amine HCl salt was filtered off and dried under high vacuum to afford a white solid.

Step 4: Preparation of N-[(1S)-1-cyano-2-(4-iodophenyl)ethyl]-4-fluoro-N$^2$-{(1S)-2,2,2-trifluoro-1-[4'-(methylsulfonyl)biphenyl-4-yl]ethyl}-L-leucinamide Using (1S)-1-cyano-2-(4-iodophenyl)ethanaminium chloride, N-[(1S)-1-cyano-2-(4-iodophenyl)ethyl]-4-fluoro-N$^2$-{(1S)-2,2,2-trifluoro-1-[4'-(methylsulfonyl)biphenyl-4-yl]ethyl}-L-leucinamide was prepared following the procedure described in step 4 of Example 2.

Step 5: Preparation of (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-cyano-phenyl)-ethyl]-amide To N-[(1S)-1-cyano-2-(4-iodophenyl)ethyl]-4-fluoro-N$^2$-{(1S)-2,2,2-trifluoro-1-[4'-(methylsulfonyl)biphenyl-4-yl]ethyl}-L-leucinamide (1 eq) in DMF (0.1 M) were added Pd$_2$(dba)$_3$ (0.05 eq), dppf (0.05 eq), water (10 eq) and zinc cyanide (2.5 eq). N$_2$ was bubbled into the mixture for 5 minutes and the mixture was then heated to 90° C. for 2 h. The reaction mixture was cooled and diluted with EtOAc and saturated aqueous ammonium chloride, the aqueous layer was extracted with EtOAc. The combined organic layers were washed with brine and water, filtered and concentrated. The crude compound was purified by automated SiO$_2$ flash chromatography system using solvent gradient of 40% EtOAc/Hex to 100% EtOAc/Hex.

M−1 (−ESI)=612.9

Example 4

Synthesis of (2S)—N-[(1R)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide

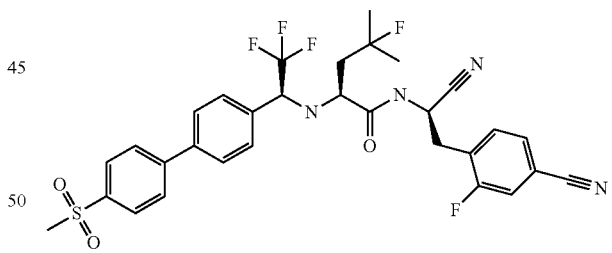

Step 1: Preparation of (2S)—N-[(1R)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide Using 4-[(2R)-(2-amino-2-cyanoethyl)]-3-fluorobenzonitrile prepared following step 3 of Example 2, (2S)—N-[(1R)-1-cyano-2-(4-cyano-2-fluorophenyl)ethyl]-4-fluoro-4-methyl-2-({(1S)-2,2,2-trifluoro-1-[4'-(methylsulfonyl)biphenyl-4-yl]ethyl}amino) pentanamide was prepared following the procedure described in step 4 of Example 2.

M+1 (+ESI)=633.3

Example 5

Synthesis of (S)-4-Fluoro-4-methyl-2-[(S)-2,2,2-trifluoro-1-(4'-methanesulfonyl-biphenyl-4-yl)-ethylamino]-pentanoic acid [2-(2-chloro-4-cyano-phenyl)-1-cyano-ethyl]-amide

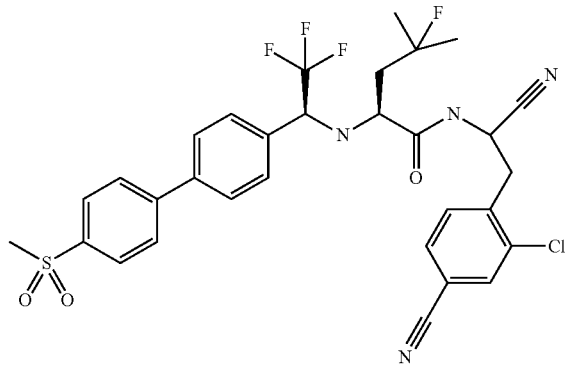 [SMILES: CC(C)(F)C[C@H](N[C@@H](c1ccc(-c2ccc(S(C)(=O)=O)cc2)cc1)C(F)(F)F)C(=O)NC(C#N)Cc1ccc(C#N)cc1Cl]

(S)-4-Fluoro-4-methyl-2-[(S)-2,2,2-trifluoro-1-(4'-methanesulfonyl-biphenyl-4-yl)-ethylamino]-pentanoic acid [2-(2-chloro-4-cyano-phenyl)-1-cyano-ethyl]-amide was prepared from 3-chloro-4-methylbenzonitrile by following procedure described in Example 2.
M+1 (+ESI)=648.9

Example 6

Synthesis of (S)-2-[(S)-1-(2'-Chloro-4'-methanesulfonyl-biphenyl-4-yl)-2,2,2-trifluoro-ethylamino]-4-fluoro-4-methyl-pentanoic acid [2-(2-chloro-4-cyano-phenyl)-1-cyano-ethyl]-amide

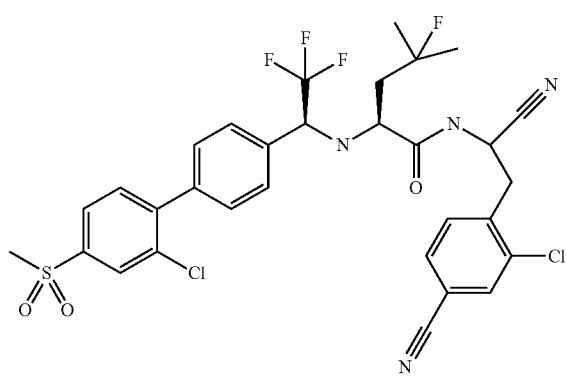 [SMILES: CC(C)(F)C[C@H](N[C@@H](c1ccc(-c2ccc(S(C)(=O)=O)cc2Cl)cc1)C(F)(F)F)C(=O)NC(C#N)Cc1ccc(C#N)cc1Cl]

Step 1: Preparation of 2-chloro-1-iodo-4-(methylsulfonyl)benzene

2-Chloro-4-Methylsulfonylaniline in a 1:1:3 mixture (0.4 M) of Acetic Acid, Hydrochloric Acid, 37% and Water was cooled to 0° C. and slowly treated with a 4 M solution of sodium nitrite in water. The reaction was stirred at 5° C. for 30 minutes then treated dropwise with a 2M solution of potassium iodide in water. The reaction evolved a gas and turned brown. The reaction was stirred 15 minutes at 0° C., 40 minutes at rt and 1 h at 60° C. The brown solid was filtered, dissolved in ethyl acetate and the solution washed with acidified sodium thiosulfate and then brine. The organic phase was dried over magnesium sulfate and concentrated under reduced pressure. During evaporation, a precipitate appeared and was filtered. The mother liquors were evaporated further and 2 more crops were collected. The last mother liquor was transferred with diethyl ether and upon evaporation yields more products.

Step 2: Preparation of ethyl 4-fluoro-N-{(1S)-2,2,2-trifluoro-1-[4-(4,4,5,5-tetramethyl-1,3,2-dioxaborolan-2-yl)phenyl]ethyl}-L-leucinate To a solution of ethyl ester of N-[(1S)-1-(4-bromophenyl)-2,2,2-trifluoroethyl]-4-fluoro-L-leucine described in U.S. Pat. No. 7,407,959 (hereby incorporated by reference I its entirety) were added Potassium Acetate and Bis(Pinacolato) Diboron in DMF (0.2 M). The mixture was degassed for 5 minutes with nitrogen bubbling. Then Pd(dppf)Cl$_2$ was added and the reaction immersed in an oil bath at 70° C. for the night. The reaction was concentrated under reduced pressure to one third of its volume approximately and filtered onto silica gel eluting with ethyl acetate. The filtrate was concentrated and used as such in the next reaction.

Step 3: Preparation of ethyl N-{(1S)-1-[2'-chloro-4'-(methylsulfonyl)biphenyl-4-yl]-2,2,2-trifluoroethyl}-4-fluoro-L-leucinate Ethyl 4-fluoro-N-{(1S)-2,2,2-trifluoro-1-[4-(4,4,5,5-tetramethyl-1,3,2-dioxaborolan-2-yl)phenyl]ethyl}-L-leucinate, 2-chloro-1-iodo-4-(methylsulfonyl)benzene (and 2M aqueous Sodium Carbonate in DMF (0.2M) were degassed with nitrogen bubbling for 3 minutes. Then PdCl2(dppf)-CH$_2$Cl$_2$ adduct was added in one portion and the flask immersed in an oil bath at 70° C. for the night. The reaction media was cooled and poured onto water. The aqueous layer was extracted with EtOAc. The combined organic layers were dried with brine and water, dried over magnesium sulfate, filtered and concentrated.

Step 4: Preparation of N-{(1S)-1-[2'-chloro-4'-(methylsulfonyl)biphenyl-4-yl]-2,2,2-trifluoroethyl}-4-fluoro-L-leucine To a solution of ethyl N-{(1S)-1-[2'-chloro-4'-(methylsulfonyl)biphenyl-4-yl]-2,2,2-trifluoroethyl}-4-fluoro-L-leucinate in a 3:1:1 mixture (0.1 M) of tetrahydrofuran, water and ethanol was added solid Lithium Hydroxide. The reaction was stirred for 64 h at room temperature and heated for one hour at 38° C. after which TLC analysis indicated disappearance of starting material. The reaction was cooled and treated with aqueous pH 5 NaH2PO4 solution and brine and then 1N aqueous HCL until pH 2. The phases were separated and the organic phase was washed with aqueous pH 5 NaH2PO4 solution and brine.

The organic layer was separated, dried over magnesium sulfate, filtered and concentrated.

Step 5: Preparation of (S)-2-[(S)-1-(2'-Chloro-4'-methanesulfonyl-biphenyl-4-yl)-2,2,2-trifluoro-ethylamino]-4-fluoro-4-methyl-pentanoic acid [2-(2-chloro-4-cyano-phenyl)-1-cyano-ethyl]-amide (S)-2-[(S)-1-(2'-Chloro-4'-methanesulfonyl-biphenyl-4-yl)-2,2,2-trifluoro-ethylamino]-4-fluoro-4-methyl-pentanoic acid [2-(2-chloro-4-cyano-phenyl)-1-cyano-ethyl]-amide was prepared from N-{(1S)-1-[2'-chloro-4'-(methylsulfonyl)biphenyl-4-yl]-2,2,2-trifluoroethyl}-4-fluoro-L-leucine and 4-(2-amino-2-cyanoethyl)-3-chlorobenzonitrile by following procedures as in step 4 of Example 2.

M+1 (+ESI)=683.0

Example 7

Synthesis of (S)-2-[(S)-1-(2'-Chloro-4'-methane-sulfonyl-biphenyl-4-yl)-2,2,2-trifluoro-ethylamino]-4-fluoro-4-methyl-pentanoic acid [1-cyano-2-(4-cyano-2-fluoro-phenyl)-ethyl]-amide

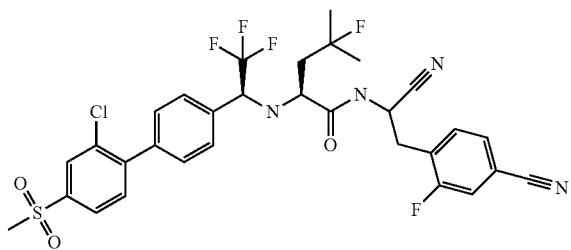 [SMILES: CC(C)(F)C[C@H](N[C@@H](c1ccc(-c2ccc(S(C)(=O)=O)cc2Cl)cc1)C(F)(F)F)C(=O)NC(C#N)Cc1ccc(C#N)cc1F]

(S)-2-[(S)-1-(2'-Chloro-4'-methanesulfonyl-biphenyl-4-yl)-2,2,2-trifluoro-ethylamino]-4-fluoro-4-methyl-pentanoic acid [1-cyano-2-(4-cyano-2-fluoro-phenyl)-ethyl]-amide was prepared from N-{(1S)-1-[2'-chloro-4'-(methylsulfonyl)biphenyl-4-yl]-2,2,2-trifluoroethyl}-4-fluoro-L-leucine and 4-[(2S)-(2-amino-2-cyanoethyl)]-3-fluorobenzonitrile using procedure described in Example 6.

M-1 (-ESI)=665.7

Example 8

Synthesis of (S)-4-Methyl-2-[(S)-2,2,2-trifluoro-1-(4'-methanesulfonyl-biphenyl-4-yl)-ethylamino]-pentanoic acid [1-cyano-2-(4-cyano-phenyl)-ethyl]-amide

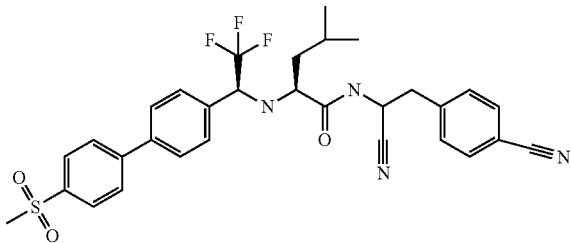 [SMILES: CC(C)C[C@H](N[C@@H](c1ccc(-c2ccc(S(C)(=O)=O)cc2)cc1)C(F)(F)F)C(=O)NC(C#N)Cc1ccc(C#N)cc1]

(S)-4-Methyl-2-[(S)-2,2,2-trifluoro-1-(4'-methanesulfonyl-biphenyl-4-yl)-ethylamino]-pentanoic acid [1-cyano-2-(4-cyano-phenyl)-ethyl]-amide was prepared from methyl L-leucinate and (1S)-1-cyano-2-(4-iodophenyl)ethanaminium chloride using procedure described in Example 1 steps 7-9 and Example 3 step 5.

M-1 (-ESI)=595.1

Example 9

Synthesis of (S)-2-[(S)-1-(4-Bromo-phenyl)-2,2,2-trifluoro-ethylamino]-4-methyl-pentanoic acid [(S)-1-cyano-2-(4-methanesulfonyl-phenyl)-ethyl]-amide

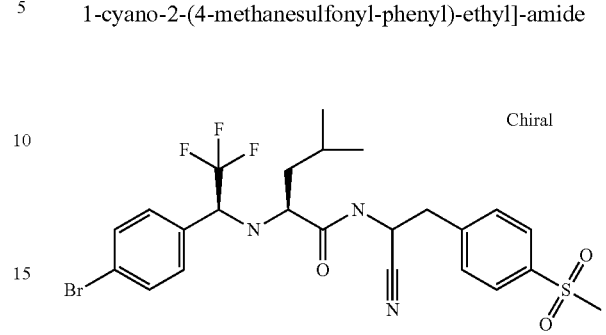

Step 1: Preparation of $N^2$-[(1S)-1-(4-bromophenyl)-2,2,2-trifluoroethyl]-N-[(1S)-1-cyano-2-(4-iodophenyl)ethyl]-L-leucinamide $N^2$-[(1S)-1-(4-bromophenyl)-2,2,2-trifluoroethyl]-N-[(1S)-1-cyano-2-(4-iodophenyl)ethyl]-L-leucinamide was prepared from methyl L-leucinate and (1S)-1-cyano-2-(4-iodophenyl)ethanaminium chloride using procedures described in Example 8.

Step 2: Preparation of (S)-2-[(S)-1-(4-Bromo-phenyl)-2,2,2-trifluoro-ethylamino]-4-methyl-pentanoic acid [(S)-1-cyano-2-(4-methanesulfonyl-phenyl)-ethyl]-amide To $N^2$-[(1S)-1-(4-bromophenyl)-2,2,2-trifluoroethyl]-N-[(1S)-1-cyano-2-(4-iodophenyl)ethyl]-L-leucinamide (1 eq) in DMSO (0.3 M) were added methane sulfonic acid sodium salt (2 eq) and copper iodide (3 eq) and the mixture was stirred at 100° C. for 2 h. The reaction mixture was cooled and diluted with EtOAc. The organic layer was washed with brine and water, dried over $Na_2SO_4$, filtered and concentrated. The crude compound was purified by automated $SiO_2$ flash chromatography system using solvent gradient of 40% EtOAc/Hex to 100% EtOAc/Hex.

M-1 (-ESI)=572.3

Example 10

Synthesis of 1-{4'-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid amide

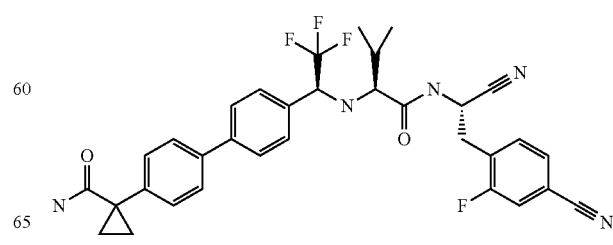

Step 1: Preparation of N²-[(1S)-1-(4-bromophenyl)-2,2,2-trifluoroethyl]-N-[(1S)-1-cyano-2-(4-cyano-2-fluorophenyl)ethyl]-L-valinamide N²-[(1S)-1-(4-bromophenyl)-2,2,2-trifluoroethyl]-N-[(1S)-1-cyano-2-(4-cyano-2-fluorophenyl)ethyl]-L-valinamide was prepared from methyl L-valinate and (1S)-1-cyano-2-(4-iodophenyl)ethanaminium chloride using procedures described in Examples 1 and 2.

Step 2: Preparation of 1-[4'-((1S)-1-{[(1S)-1-({[(1S)-1-cyano-2-(4-cyano-2-fluorophenyl)ethyl]amino}carbonyl)-2-methylpropyl]amino}-2,2,2-trifluoroethyl)biphenyl-4-yl]cyclopropanecarboxylic acid To N²-[(1S)-1-(4-bromophenyl)-2,2,2-trifluoroethyl]-N-[(1S)-1-cyano-2-(4-cyano-2-fluorophenyl)ethyl]-L-valinamide (1 eq) in DMF (0.1M) were added 1-[4-(dihydroxyboryl)phenyl]cyclopropanecarboxylic acid (1.2 eq), Pd(dppf)Cl₂ (0.05 eq) and 2M aqueous sodium carbonate (3 eq). The mixture was degassed by nitrogen bubbling for 5 min and heated to 90° C. for 2 h. The reaction mixture was cooled and diluted with EtOAc and 3N HCl was added to acidify the reaction mixture to pH 5. The aqueous layer was extracted with EtOAc. The combined organic layers were washed with brine and water, dried over Na₂SO₄ filtered and concentrated. The crude compound was purified by automated SiO₂ flash chromatography system using solvent gradient of 40% EtOAc/Hex to 100% EtOAc/Hex.

Step 2: Preparation of 1-{4'-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid amide To 1-[4'4(1S)-1-{[(1S)-1-({[(1S)-1-cyano-2-(4-cyano-2-fluorophenyl)ethyl]amino}carbonyl)-2-methylpropyl]amino}-2,2,2-trifluoroethyl)biphenyl-4-yl]cyclopropanecarboxylic acid (1 eq)) in DMF (0.15M) at 0° C. was added HATU (1.2 eq). 30% aqueous solution of NH₄OH (3 eq) was then slowly added and the reaction mixture was then stirred at 0° C. for 2 h. The mixture was poured into a saturated aqueous solution of sodium hydrogen bicarbonate and the aqueous layer was extracted with EtOAc. The combined organic layers were washed with brine and water, dried over Na₂SO₄, filtered and concentrated. The crude compound was purified by automated SiO₂ flash chromatography system using solvent gradient of 40% EtOAc/Hex to 100% EtOAc/Hex.
M+1 (+HI)=605.641

Example 11

Synthesis of (S)—N—[(S)-Cyano-(4-cyano-2-fluoro-benzyl)-methyl]-2-{(S)-1-[4'-((R)-2,2-difluoro-1-hydroxy-ethyl)-biphenyl-4-yl]-2,2,2-trifluoro-ethylamino}-3-methyl-butyramide

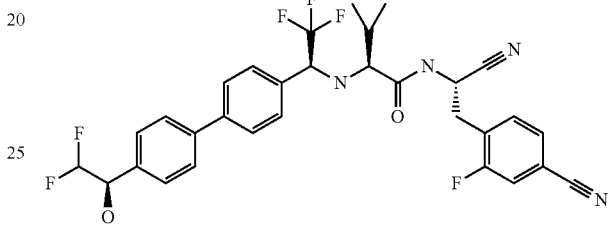

(S)—N—[(S)-Cyano-(4-cyano-2-fluoro-benzyl)-methyl]-2-{(S)-1-[4'-((R)-2,2-difluoro-1-hydroxy-ethyl)-biphenyl-4-yl]-2,2,2-trifluoro-ethylamino}-3-methyl-butyramide was prepared from N²-[(1S)-1-(4-bromophenyl)-2,2,2-trifluoroethyl]-N-[(1S)-1-cyano-2-(4-cyano-2-fluorophenyl)ethyl]-L-valinamide and (1R)-2,2-difluoro-1-[4-(4,4,5,5-tetramethyl-1,3,2-dioxaborolan-2-yl)phenyl]ethanol (described in U.S. Pat. No. 7,407,959, hereby incorporated by reference in its entirety.) using procedure described in step 2 of Example 10.
M+1 (+ESI)=603.2

Using the methods described above, the following compounds were prepared:

TABLE 1

| Ex. | Compound | Compound Name | Characterization data | Assay IC50 (nM) |
|---|---|---|---|---|
| 1 | 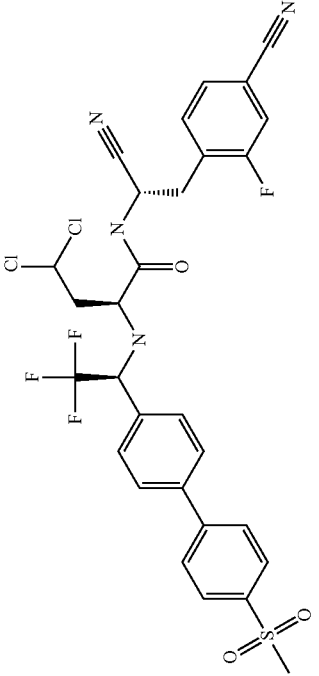 | (S)-4,4-Dichloro-N-[(S)-cyano-(4-cyano-2-fluoro-benzyl)-methyl]-2-[(S)-2,2,2-trifluoro-1-(4'-methanesulfonyl-biphenyl-4-yl)-ethylamino]-butyramide | M + 1, +ESI = 655 and 657 | 0.14 |
| 2 | 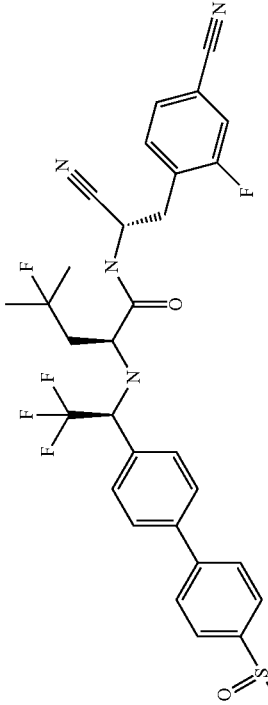 | (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-cyano-2-fluoro-phenyl)-ethyl]-amide | M + 1, +ESI = 633.2 | 0.95 |
| 3 | 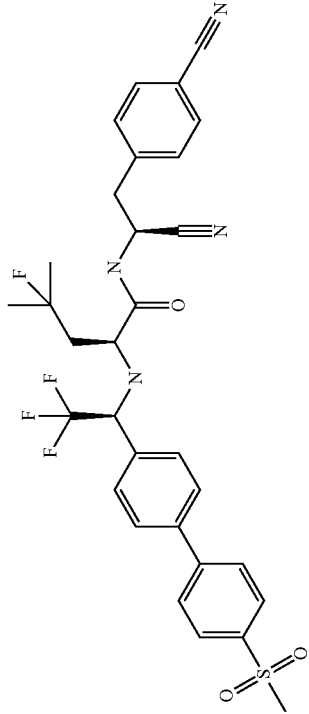 | (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-cyano-phenyl)-ethyl]-amide | M − 1, −ESI = 612.9 | 1.5 |

TABLE 1-continued
| Ex. | Compound | Compound Name | Characterization data | Assay IC50 (nM) |
|---|---|---|---|---|
| 4 | 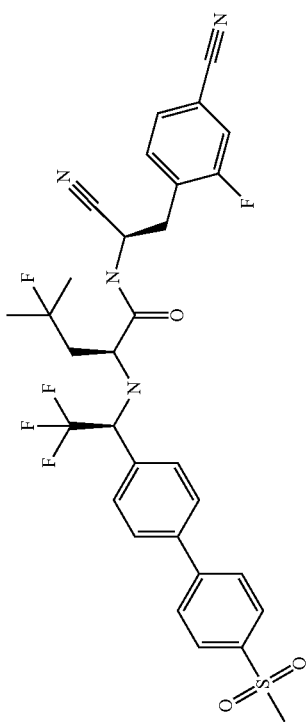 | (S)-4-Fluoro-4-methyl-2-[(S)-2,2,2-trifluoro-1-(4'-methanesulfonyl-biphenyl-4-yl)-ethylamino]-pentanoic acid [(R)-1-cyano-2-(4-cyano-2-fluoro-phenyl)-ethyl]-amide | M + 1, +ESI = 633.3 | 22.2 |
| 5 | 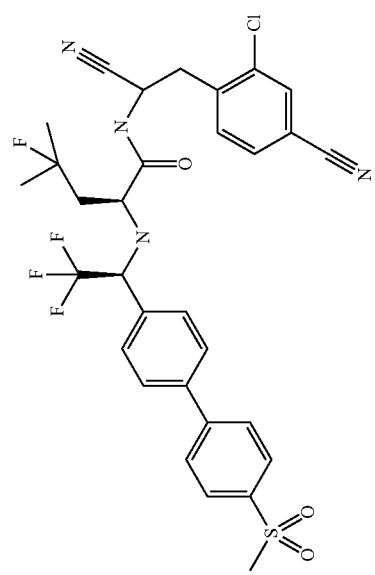 | (S)-4-Fluoro-4-methyl-2-[(S)-2,2,2-trifluoro-1-(4'-methanesulfonyl-biphenyl-4-yl)-ethylamino]-pentanoic acid [2-(2-chloro-4-cyano-phenyl)-1-cyano-ethyl]-amide | M + 1, +ESI = 648.9 | |

TABLE 1-continued

| Ex. | Compound | Compound Name | Characterization data | Assay IC50 (nM) |
|---|---|---|---|---|
| 6 | | (S)-2-[(S)-1-(2'-Chloro-4'-methanesulfonyl-biphenyl-4-yl)-2,2,2-trifluoro-ethylamino]-4-fluoro-4-methyl-pentanoic acid [2-(2-chloro-4-cyano-phenyl)-1-cyano-ethyl]-amide | M + 1, +ESI = 683.0 | 1.2 |
| 7 | | (S)-2-[(S)-1-(2'-Chloro-4'-methanesulfonyl-biphenyl-4-yl)-2,2,2-trifluoro-ethylamino]-4-fluoro-4-methyl-pentanoic acid [1-cyano-2-(4-cyano-2-fluoro-phenyl)-ethyl]-amide | M − 1, −ESI = 665.7 | 0.9 |
| 8 | | (S)-4-Methyl-2-[(S)-2,2,2-trifluoro-1-(4'-methanesulfonyl-biphenyl-4-yl)-ethylamino]-pentanoic acid [1-cyano-2-(4-cyano-phenyl)-ethyl]-amide | M − 1, −ESI = 595.1 | 0.2 |

TABLE 1-continued

| Ex. | Compound | Compound Name | Characterization data | Assay IC50 (nM) |
|---|---|---|---|---|
| 9 | | (S)-2-[(S)-1-(4-Bromo-phenyl)-2,2,2-trifluoro-ethylamino]-4-methyl-pentanoic acid [(S)-1-cyano-2-(4-methanesulfonyl-phenyl)-ethyl]-amide | M − 1, −ESI = 572.3 | 0.6 |
| 10 | | 1-{4′-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl}-cyclopropanecarboxylic acid amide | M + 1, +ESI = 606.2 | 0.15 |
| 11 | | (S)-N-[(S)-Cyano-(4-cyano-2-fluoro-benzyl)-methyl]-2-{(S)-1-[4′-((R)-2,2-difluoro-1-hydroxy-ethyl)-biphenyl-4-yl]-2,2,2-trifluoro-ethylamino}-3-methyl-butyramide | M + 1, +ESI = 603.2 | 0.33 |

TABLE 1-continued

| Ex. | Compound | Compound Name | Characterization data | Assay IC50 (nM) |
|---|---|---|---|---|
| 12 | | (S)-4-Fluoro-4-methyl-2-[(S)-2,2,2-trifluoro-1-(4'-methanesulfonyl-biphenyl-4-yl)-ethylamino]-pentanoic acid ((S)-benzyl-cyano-methyl)-amide | M + 1, +ESI = 590.2 | 8.1 |
| 13 | | (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid ((S)-benzyl-cyano-methyl)-amide | M + 1, +ESI = 592.2 | 8.1 |
| 14 | | (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-pyridin-3-yl-phenyl)-ethyl]-amide | M + 1, +ESI = 667.0 | 7 |

TABLE 1-continued

| Ex. | Compound | Compound Name | Characterization data | Assay IC50 (nM) |
|---|---|---|---|---|
| 15 | | 4-{(S)-2-Cyano-2-[(S)-4-fluoro-4-methyl-2-[(S)-2,2,2-trifluoro-1-(4'-methanesulfonyl-biphenyl-4-yl)-ethylamino]-pentanoylamino]-ethyl)-benzoic acid ethyl ester | M + 1, +ESI = 662.3 | 4.4 |
| 16 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(4-fluoro-benzyl)-methyl]-amide | M + 1, +ESI = 608.2 | 6.1 |
| 17 | | (S)-Fluoro-4-methyl-2-[(S)-2,2,2-trifluoro-1-(4'-methanesulfonyl-biphenyl-4-yl)-ethylamino]-pentanoic acid [(S)-1-cyano-2-(2-fluoro-phenyl)-ethyl]-amide | M − 1, −ESI = 606.2 | 0.9 |

TABLE 1-continued

| Ex. | Compound | Compound Name | Characterization data | Assay IC50 (nM) |
|---|---|---|---|---|
| 18 | | (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(2,4-dichloro-phenyl)-ethyl]-amide | M + 1, +ESI = 658.1 and 661.2 | 1.3 |
| 19 | | (S)-4-Fluoro-4-methyl-2-[(S)-2,2,2-trifluoro-1-(4'-methanesulfonyl-biphenyl-4-yl)-ethylamino]-pentanoic acid [(S)-1-cyano-2-(4-trifluoromethyl-phenyl)-ethyl]-amide | M − 1, −ESI = 656.2 | 12.4 |
| 20 | | (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [(S)-1-cyano-2-(4-methanesulfonyl-phenyl)-ethyl]-amide | M − 1, −ESI = 668.4 | 8.4 |

TABLE 1-continued

| Ex. | Compound | Compound Name | Characterization data | Assay IC50 (nM) |
|---|---|---|---|---|
| 21 | | (S)-2-[(S)-1-(4-Bromo-phenyl)-2,2,2-trifluoro-ethylamino]-4-methyl-pentanoic acid [(S)-1-cyano-2-(4-cyano-phenyl)-ethyl]-amide | M − 1, −ESI = 521.5 | 0.94 |
| 22 | | (S)-4-Fluoro-4-methyl-2-[(S)-2,2,2-trifluoro-1-(4'-methanesulfonyl-biphenyl-4-yl)-ethylamino]-pentanoic acid [(R,S)-1-cyano-2-(4-cyano-2-fluoro-phenyl)-ethyl]-amide | M − 1, −ESI = 631.3 | 1.2 |
| 23 | | (S)-N-(Benzyl-cyano-methyl)-4,4-dichloro-2-[(S)-2,2,2-trifluoro-1-(4'-methanesulfonyl-biphenyl-4-yl)-ethylamino]-butyramide | M + 1, +ESI = 612.1 and 614.1 | 0.1 |

TABLE 1-continued

| Ex. | Compound | Compound Name | Characterization data | Assay IC50 (nM) |
|---|---|---|---|---|
| 24 | | (S)-4-Fluoro-4-methyl-2-[(S)-2,2,2-trifluoro-1-(4-methanesulfonyl-[1,1';4',1'']terphenyl-4''-yl)-ethylamino]-pentanoic acid ((S)-benzyl-cyano-methyl)-amide | M + 1, +ESI = 666.2 | 16 |
| 25 | | (S)-4-Fluoro-4-methyl-2-[(S)-2,2,2-trifluoro-1-(4'-methanesulfinyl-biphenyl-4-yl)-ethylamino]-pentanoic acid [(S)-1-cyano-2-(4-cyano-2-fluoro-phenyl)-ethyl]-amide | M − 1, −ESI = 615.1 | 0.75 |
| 26 | | (S)-4-Fluoro-4-methyl-2-[(S)-2,2,2-trifluoro-1-(4'-methylsulfanyl-biphenyl-4-yl)-ethylamino]-pentanoic acid [(S)-1-cyano-2-(4-cyano-2-fluoro-phenyl)-ethyl]-amide | M − 1, −ESI = 599.2 | 4.2 |

TABLE 1-continued

| Ex. | Compound | Compound Name | Characterization data | Assay IC50 (nM) |
|---|---|---|---|---|
| 27 | | (S)-2-{(S)-1-[4'-(1-Cyano-cyclopropyl)-biphenyl-4-yl]-2,2,2-trifluoro-ethylamino}-4-fluoro-4-methyl-pentanoic acid ((S)-1-cyano-2-phenyl-ethyl)-amide | M + 1, +ESI = 577.2 | 10.4 |
| 28 | | (S)-4-Fluoro-4-methyl-2-((S)-2,2,2-trifluoro-1-{4'-[1-(morpholine-4-carbonyl)-cyclopropyl]-biphenyl-4-yl}-ethylamino)-pentanoic acid ((S)-1-cyano-2-phenyl-ethyl)-amide | M + 1, +ESI = 665.2 | 3.1 |
| 29 | | (S)-4-Fluoro-4-methyl-2-((S)-2,2,2-trifluoro-1-[4'-(1-[1,2,4]oxadiazol-3-yl-cyclopropyl)-biphenyl-4-yl]-ethylamino)-pentanoic acid ((S)-1-cyano-2-phenyl-ethyl)-amide | M + 1, +ESI = 620.2 | 20 |

TABLE 1-continued

| Ex. | Compound | Compound Name | Characterization data | Assay IC50 (nM) |
|---|---|---|---|---|
| 30 | | 1-(4'-{(S)-1-[(S)-1-Cyano-2-phenyl-ethylcarbamoyl)-3-fluoro-3-methyl-butylamino]-2,2,2-trifluoro-ethyl}-biphenyl-4-yl)-cyclopropanecarboxylic acid amide | M + 1, +ESI = 595.2 | 2.9 |
| 31 | | (S)-4-Fluoro-4-methyl-2-[(S)-2,2,2-trifluoro-1-(4'-sulfamoyl-biphenyl-4-yl)-ethylamino]-pentanoic acid ((S)-1-cyano-2-phenyl-ethyl)-amide | M + 1, +ESI = 591.2 | 16 |
| 32 | | (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [(S)-cyano-(4-cyano-2-fluoro-benzyl)-methyl]-amide | M + 1, +ESI = 635.2 | 0.9 |

TABLE 1-continued

| Ex. | Compound | Compound Name | Characterization data | Assay IC50 (nM) |
|---|---|---|---|---|
| 33 | | (S)-4-Fluoro-4-methyl-2-[(S)-2,2,2-trifluoro-1-(4'-methanesulfonyl-biphenyl-4-yl)-ethylamino]-pentanoic acid [cyano-(2-fluoro-4-trifluoromethyl-benzyl)-methyl]-amide | M + 1, +ESI = 676.2 | 3.5 |
| 34 | | (S)-4-Fluoro-4-methyl-2-[(S)-2,2,2-trifluoro-1-(4'-methanesulfonyl-biphenyl-4-yl)-ethylamino]-pentanoic acid [cyano-(2,4-difluoro-benzyl)-methyl]-amide | M + 1, +ESI = 626.2 | 2.6 |
| 35 | | (S)-4-Fluoro-4-methyl-2-[(S)-2,2,2-trifluoro-1-[4-(1-methyl-1H-pyrrol-2-yl)-phenyl]-ethylamino]-pentanoic acid ((S)-1-cyano-2-phenyl-ethyl)-amide | M + 1, +ESI = 515.2 | 12.2 |

TABLE 1-continued

| Ex. | Compound | Compound Name | Characterization data | Assay IC50 (nM) |
|---|---|---|---|---|
| 36 | | (S)-4-Fluoro-4-methyl-2-[(S)-2,2,2-trifluoro-1-(4'-pyridin-4-yl-biphenyl-4-yl)-ethylamino]-pentanoic acid ((S)-1-cyano-2-phenyl-ethyl)-amide | M + 1, +ESI = 589.2 | 7.5 |
| 37 | | (S)-2-{(S)-1-[4'-((R)-2,2-Difluoro-1-hydroxy-ethyl)-biphenyl-4-yl]-2,2,2-trifluoro-ethylamino}-4-fluoro-4-methyl-pentanoic acid [cyano-(2-fluoro-4-trifluoromethyl-benzyl)-methyl]-amide | M + 1, +ESI = 678.2 | 9.3 |
| 38 | | 1-[4'-((S)-1-{(S)-1-Cyano-2-(4-cyano-2-fluoro-phenyl)-ethylcarbamoyl]-3-fluoro-3-methyl-butylamino}-2,2,2-trifluoro-ethyl)-biphenyl-4-yl]-cyclopropanecarboxylic acid amide | M + 1, +ESI = 638.2 | 0.3 |

TABLE 1-continued

| Ex. | Compound | Compound Name | Characterization data | Assay IC50 (nM) |
|---|---|---|---|---|
| 39 | | (S)-4-Fluoro-4-methyl-2-[(S)-2,2,2-trifluoro-1-(4'-pyridin-4-yl-biphenyl-4-yl)-ethylamino]-pentanoic acid [(S)-1-cyano-2-(4-cyano-2-fluoro-phenyl)-ethyl]-amide | M + 1, +ESI = 632.2 | 0.6 |
| 40 | | (S)-2-[(S)-1-(4-Bromo-phenyl)-2,2,2-trifluoro-ethylamino]-N-((S)-1-cyano-2-phenyl-ethyl)-3-methyl-butyramide | M − 1, −ESI = 481.1 | 10.5 |
| 41 | | (S)-N-((S)-1-Cyano-2-phenyl-ethyl)-3-methyl-2-[(S)-2,2,2-trifluoro-1-(4'-methanesulfonyl-biphenyl-4-yl)-ethylamino]-butyramide | M + 1, +ESI = 558.1 | 1.7 |

TABLE 1-continued

| Ex. | Compound | Compound Name | Characterization data | Assay IC50 (nM) |
|---|---|---|---|---|
| 42 | | (S)-4-Fluoro-4-methyl-2-((S)-2,2,2-trifluoro-1-[4'-(2-hydroxy-2-methyl-propyl)-biphenyl-4-yl]-ethylamino]-pentanoic acid [(S)-1-cyano-2-(4-cyano-2-fluoro-phenyl)-ethyl]-amide | M + 1, +ESI = 627.3 | 0.9 |
| 43 | | (S)-4-Fluoro-4-methyl-2-((S)-2,2,2-trifluoro-1-{4'-[1-(morpholine-4-carbonyl)-cyclopropyl]-biphenyl-4-yl}-ethylamino)-pentanoic acid [(S)-1-cyano-2-(4-cyano-2-fluoro-phenyl)-ethyl]-amide | M + 1, +ESI = 708.2 | 0.35 |
| 44 | | (S)-2-[(S)-1-(4-Bromo-phenyl)-2,2,2-trifluoro-ethylamino]-4-fluoro-4-methyl-pentanoic acid [(S)-1-cyano-2-(4-cyano-2-fluoro-phenyl)-ethyl]-amide | M + 1, +ESI = 557.1 and 558.1 | 9.4 |

TABLE 1-continued

| Ex. | Compound | Compound Name | Characterization data | Assay IC50 (nM) |
|---|---|---|---|---|
| 45 | | (S)-4-Fluoro-4-methyl-2-[(S)-2,2,2-trifluoro-1-[4'-(1-oxy-pyridin-4-yl)-biphenyl-4-yl]-ethylamino}-pentanoic acid ((S)-1-cyano-2-phenyl-ethyl)-amide | M + Na, +ESI = 627.2 | 7.8 |
| 46 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(2-fluoro-4-trifluoromethyl-benzyl)-methyl]-amide | M + 1, +ESI = 676.1 | 1.5 |
| 47 | | 4-[4'-((S)-1-{[(S)-1-{[((S)-Benzyl-cyano-methyl)-carbamoyl]-2-methyl-propylamino}-2,2,2-trifluoro-ethyl)-biphenyl-4-yl]-piperazin-1-ium; chloride | M − 1, −ESI = 599.3 | 0.1 |

TABLE 1-continued

| Ex. | Compound | Compound Name | Characterization data | Assay IC50 (nM) |
|---|---|---|---|---|
| 48 | | 1-[4'-((S)-1-{(S)-1-[((S)-Benzyl-cyano-methyl)-carbamoyl]-2-methyl-propylamino}-2,2,2-trifluoro-ethyl)-biphenyl-4-yl]-cyclopropanecarboxylic acid amide | M + 1, +ESI = 563.2 | 0.7 |
| 49 | | (S)-N-((S)-Benzyl-cyano-methyl)-3-methyl-2-[(S)-2,2,2-trifluoro-1-(4-pyridin-4-yl-phenyl)-ethylamino]-butyramide | M + 1, +ESI = 481.2 | 5.6 |
| 50 | | (S)-N-((S)-Benzyl-cyano-methyl)-2-{(S)-1-[4'-((R)-2,2-difluoro-1-hydroxy-ethyl)-biphenyl-4-yl]-2,2,2-trifluoro-ethylamino}-3-methyl-butyramide | M + 1, +ESI = 560.2 | 3.2 |

TABLE 1-continued

| Ex. | Compound | Compound Name | Characterization data | Assay IC50 (nM) |
|---|---|---|---|---|
| 51 | | (S)-N-[(S)-Cyano-(4-cyano-2-fluoro-benzyl)-methyl]-3-methyl-2-[(S)-2,2,2-trifluoro-1-(4'-methanesulfonyl-biphenyl-4-yl)-ethylamino]-butyramide | M − 1, −ESI = 599.1 | 0.3 |
| 52 | | 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid (2-hydroxy-ethyl)-amide | M + 1, +ESI = 639.3 | 2.8 |
| 53 | | ({1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarbonyl}-amino)-acetic acid methyl ester | M + 1, +ESI = 667.2 | 3.1 |

TABLE 1-continued

| Ex. | Compound | Compound Name | Characterization data | Assay IC50 (nM) |
|---|---|---|---|---|
| 54 | | 1-[4'-((S)-1-{(S)-Benzyl-cyanomethyl)-carbamoyl]-3-fluoro-3-methyl-butylamino}-2,2,2-trifluoro-ethyl)-biphenyl-4-yl]-cyclopropanecarboxylic acid (2,2,2-trifluoro-ethyl)-amide | M + 1, +ESI = 677.2 | 9.4 |
| 55 | | 1-[4'-((S)-1-{(S)-1-[((S)-Benzyl-cyanomethyl)-carbamoyl]-3-fluoro-3-methyl-butylamino}-2,2,2-trifluoro-ethyl)-biphenyl-4-yl]-cyclopropanecarboxylic acid carbamoylmethyl-amide | M + 1, +ESI = 652.3 | 1.9 |
| 56 | | 1-[4'-((S)-1-{(S)-1-[((S)-Benzyl-cyanomethyl)-carbamoyl]-3-fluoro-3-methyl-butylamino}-2,2,2-trifluoro-ethyl)-biphenyl-4-yl]-cyclopropanecarboxylic acid cyclopropylamide | M + 1, +ESI = 635.3 | 3.7 |

TABLE 1-continued

| Ex. | Compound | Compound Name | Characterization data | Assay IC50 (nM) |
|---|---|---|---|---|
| 57 | 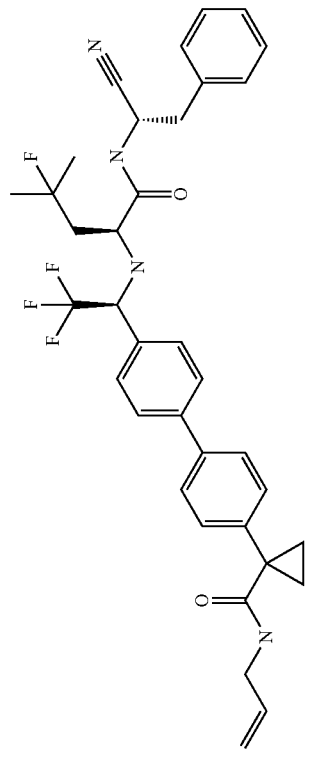 | 1-[4'-((S)-1-{(S)-1-[((S)-Benzyl-cyano-methyl)-carbamoyl]-3-fluoro-3-methyl-butylamino}-2,2,2-trifluoro-ethyl)-biphenyl-4-yl]-cyclopropanecarboxylic acid allylamide | M + 1, +ESI = 635.3 | 4.3 |
| 58 | 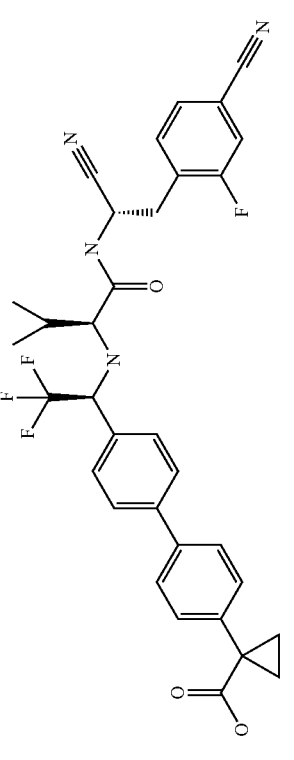 | 1-{4'-[(S)-1-{[(S)-Cyano-(4-cyano-2-fluoro-benzyl)-methyl]-carbamoyl}-2-methyl-propylamino)-2,2,2-trifluoro-ethyl]-biphenyl-4-yl]-cyclopropanecarboxylic acid | M + 1, +ESI = 607.2 | 0.3 |
| 59 | 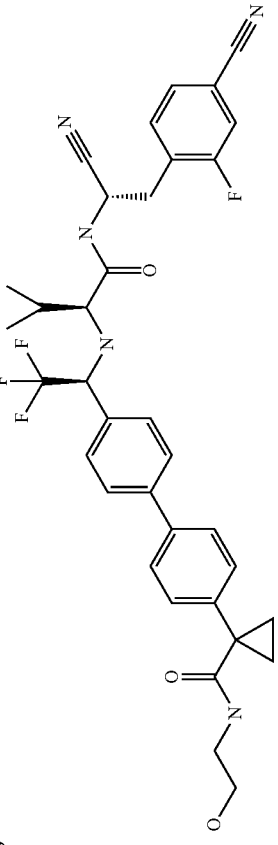 | 1-{4'-[(S)-1-((S)-1-{[(S)-Cyano-(4-cyano-2-fluoro-benzyl)-methyl]-carbamoyl}-2-methyl-propylamino)-2,2,2-trifluoro-ethyl]-biphenyl-4-yl]-cyclopropanecarboxylic acid (2-hydroxy-ethyl)-amide | M + 1, +ESI = 650.2 | 0.1 |

TABLE 1-continued

| Ex. | Compound | Compound Name | Characterization data | Assay IC50 (nM) |
|---|---|---|---|---|
| 60 | | (S)-4-Fluoro-4-methyl-2-[(S)-2,2,2-trifluoro-1-(4'-methanesulfonyl-biphenyl-4-yl)-ethylamino]-pentanoic acid ((S)-cyano-pyridin-4-ylmethyl-methyl)-amide | M + 1, +ESI = 591.2 | 6.4 |
| 61 | | (S)-N-[(S)-Cyano-(2-fluoro-4-trifluoromethyl-benzyl)-methyl]-2-[(S)-1-[4'-((R)-2,2-difluoro-1-hydroxy-ethyl)-biphenyl-4-yl]-2,2,2-trifluoro-ethylamino]-3-methyl-butyramide | M + 1, +ESI = 646.2 | 1.5 |
| 62 | | (S)-N-[(S)-Cyano-(2-fluoro-4-trifluoromethyl-benzyl)-methyl]-3-methyl-2-[(S)-2,2,2-trifluoro-1-(4'-methanesulfonyl-biphenyl-4-yl)-ethylamino]-butyramide | M + 1, +ESI = 644.2 | 0.4 |

TABLE 1-continued

| Ex. | Compound | Compound Name | Characterization data | Assay IC50 (nM) |
|---|---|---|---|---|
| 63 | | (S)-N-((S)-Benzyl-cyano-methyl)-3-cyclopropyl-2-[(S)-2,2,2-trifluoro-1-(4'-methanesulfonyl-biphenyl-4-yl)-ethylamino]-propionamide | M − 1, −ESI = 568.2 | 16.2 |
| 64 | | (S)-4-Fluoro-4-methyl-2-[(S)-2,2,2-trifluoro-1-(4'-methanesulfonyl-biphenyl-4-yl)-ethylamino]-pentanoic acid ((S)-cyano-pyridin-3-ylmethyl)-amide | M + 1, +ESI = 591.2 | 12.6 |
| 65 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-2-ylmethyl]-methyl)-amide | M + 1, +ESI = 607.2 | 15 |

TABLE 1-continued

| Ex. | Compound | Compound Name | Characterization data | Assay IC50 (nM) |
|---|---|---|---|---|
| 66 | | (S)-4-Fluoro-4-methyl-2-[(S)-2,2,2-trifluoro-1-(4'-methanesulfonyl-biphenyl-4-yl)-ethylamino]-pentanoic acid [(S)-(4-bromo-2,6-difluoro benzyl)-cyano-methyl]-amide | M − 1, −ESI = 701.7 and 704.0 | 1.6 |
| 67 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(4-cyano-2,6-difluoro-benzyl)-methyl]-amide | M + 1, +ESI = 651.1 | 0.9 |
| 68 | | (S)-N-[(S)-Cyano-(4-cyano-2-fluoro-benzyl)-methyl]-2-cyclopropyl-2-[(S)-2,2,2-trifluoro-1-(4'-methanesulfonyl-biphenyl-4-yl)-ethylamino]-acetamide | M + 1, +ESI = 599.1 | 4.4 |

TABLE 1-continued

| Ex. | Compound | Compound Name | Characterization data | Assay IC50 (nM) |
|---|---|---|---|---|
| 69 | | (S)-N-[(S)-Cyano-(4-cyano-2-fluoro-benzyl)-methyl]-2-cyclopropyl-2-{(S)-1-[4'-((R)-2,2-difluoro-1-hydroxy-ethyl)-biphenyl-4-yl]-2,2,2-trifluoro-ethylamino}-acetamide | M + 1, +ESI = 601.2 | 4.3 |
| 70 | | (S)-N-[(S)-(4-Bromo-2,6-difluoro-benzyl)-cyano-methyl]-3-methyl-2-[(S)-2,2,2-trifluoro-1-(4'-methanesulfonyl-biphenyl-4-yl)-ethylamino]-butyramide | M + 1, +ESI = 672.1 and 674.1 | 0.6 |
| 71 | | (S)-N-[(S)-(4-Bromo-2,6-difluoro-benzyl)-cyano-methyl]-2-{(S)-1-[4'-((R)-2,2-difluoro-1-hydroxy-ethyl)-biphenyl-4-yl]-2,2,2-trifluoro-ethylamino}-3-methyl-butyramide | M + 1, +ESI = 672.1 and 674.1 | 2.1 |

TABLE 1-continued

| Ex. | Compound | Compound Name | Characterization data | Assay IC50 (nM) |
|---|---|---|---|---|
| 72 | | (S)-N-[(S)-Cyano-(4-cyano-2,6-difluoro-benzyl)-methyl]-3-methyl-2-[(S)-2,2,2-trifluoro-1-(4-methanesulfonyl-biphenyl-4-yl)-ethylamino]-butyramide | M + 1, +ESI = 619.2 | 0.5 |
| 73 | | (S)-N-[(S)-Cyano-(4-cyano-2,6-difluoro-benzyl)-methyl]-2-{(S)-1-[4-((R)-2,2-difluoro-1-hydroxy-ethyl)-biphenyl-4-yl]-2,2,2-trifluoro-ethylamino}-3-methyl-butyramide | M + 1, +ESI = 621.2 | 0.7 |
| 74 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-3-ylmethyl)-methyl]-amide | M + 1, +ESI = 607.2 | 39 |

TABLE 1-continued

| Ex. | Compound | Compound Name | Characterization data | Assay IC50 (nM) |
|---|---|---|---|---|
| 75 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(1-oxy-pyridin-4-ylmethyl)-methyl]-amide | M + 1, +ESI = 607.2 | 120 |
| 76 | | (S)-4-Fluoro-4-methyl-2-[(S)-2,2,2-trifluoro-1-(4'-methanesulfonyl-biphenyl-4-yl)-ethylamino]-pentanoic acid [(S)-cyano-(2,6-difluoro-benzyl)-methyl]-amide | M + 1, +ESI = 626.2 | 7.1 |

Pharmaceutical Composition

As a specific embodiment of this invention, 100 mg of (2S)-4,4-dichloro-N-[(1S)-1-cyano-2-(4-cyano-2-fluorophenyl)ethyl]-2-({(1S)-2,2,2-trifluoro-1-[4'-(methylsulfonyl)biphenyl-4-yl]ethyl}amino)butanamide, is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

Cruzipain Assay

Serial dilutions (1/3) from 500 µM down to 0.0025 µM of test compounds were prepared in dimethyl sulfoxide (DMSO). Then an aliquot of compound in DMSO from each dilution were added in to a black 384 well polystyrene plate (Corning Cat#3573) containing 50 pM of cruzipain in assay buffer solution (NaOAc, 50 mM (pH 5.5); DTT, 5 mM; Tween-20, 0.002% v/v and DMSO 10% v/v). The assay solutions were mixed and incubated for 15 minutes at room temperature prior to the addition of 2 µM of Z-Phe-Arg-AMC substrate. Hydrolysis of the coumarin leaving group (AMC) was followed for 10 minutes using the Pherastar spectrofluorometer (BMG Labtech) set-up with the following filters: Ex λ=360 nm; Em λ=460 nm; Dichroic @ 435 nm). Percent of inhibition were calculated by fitting experimental values to standard mathematical model for dose response curve. Results of the assay ($IC_{50}$) are shown in Table 1.

Additionl assays that can be used to assess the activity of the compounds of the invention include:

*T. cruzi* Epimastigotes Assay

The epimastigote form of *T. cruzi* (Brazilian strain) is initiated in a 25 cm² flask with a cell density of 2×10⁶ epimastigotes per ml and grown in liver infusion tryptose (LIT) broth medium, supplemented with 10% newborn calf serum (Gibco) and antibiotics, at 28° C. with agitation (80 rpm) to a cell density of 0.5×10⁷ to 1×10⁷, measured with an electronic particle counter (model ZBI; Coulter Electronics Inc., Hialeah, Fla.) and by direct counting with a hemocytometer. Test compounds in DMSO ware added to the flasks when the epimastigotes cell density reaches 0.5×10⁷ to 1×10⁷ per ml then incubated for 24 to 48 h and the epimastigotes harvested during the logarithmic growth phase. The harvested epimastigotes are washed three times with 1M phosphate-buffered saline (PBS; pH 7.4) by centrifugation at 850 g for 15 minutes at 4° C. The harvested epimastigotes are reincubated in fresh LIT broth supplemented with 10% newborn calf serum and antibiotics, at 28° C. with agitation (80 rpm) and the viability of the epimistagotes evaluated for up to one week using trypan blue exclusion (light microscopy) and [³H]-thymidine incorporation assay (see below).

*T. cruzi* Trypomastigote Assay

The epimastigote forms of *T. cruzi* are grown as described above and harvested on day 14 (stationary phase) washed three times in Grace's insect medium pH 6.5 (Invitrogen or Wisent) and induced to the trypomastigote form by metacyclogenesis by the addition of fresh Grace medium supplemented with 10% fetal calf serum (FCS) and haemin (25 µg/ml) and cultured for up to five days at 28° C. To produce more trypomastigotes the culture may be used to infect a monolayer of mammalian cells such as U937 (human macrophage), J774 (mouse macrophage) or Vero (African green monkey kidney) cells up to 4 days. Trypomastigotes released to the supernatant are collected by a 3000 g centrifugation for 15 minutes and washed twice in Hank's balanced salt saline supplemented with 1 mM glucose (HBSS). Test compounds in DMSO are added to the culture of trypomastigotes with a cell density of 10⁶ per ml then incubated in RPMI-10% at 37° C. for 24 to 48 h. The trypomastigotes are harvested and reduction in number (parasite lysis) is determined using a Neubauer chamber and the $LD_{50}$ value (drug concentration that resulted in a 50% reduction in trypomastigotes when compared to an untreated control) is estimated by plotting percentage of reduction against the logarithm of drug concentration. The viability of the harvested trypomastigotes is evaluated by their ability to infect macrophages and grow in fresh media as determined by a ³H-thymidine incorporation assay (see below).

*T. cruzi* Amastigote Activity (intracellular) Assay

The epimastigotes form of *T. cruzi* is cultured in Grace's insect medium supplemented with 10% FCS and haemin (25 µg/ml) for up to fourteen days at 28° C. to induce the formation of the metacyclic form, so that about 30% of the parasite cells are in the metacyclic form. These parasite cells are harvested and used to infect confluent mammalian cells such as U937 (human macrophage), J774 (mouse macrophage) or Vero (African green monkey kidney) cell cultures grown in 24 wells microplates in MEM at 37° C. and 5% $CO_2$. After the parasitic cells are allowed to infect the macrophages, the culture media is removed and the test compounds in MEM culture medium are added to the wells and the microplates incubated for 48 h. At the end of the incubation period the media is removed and the macrophages are fixed and stained with May Grunwald Giemsa stain. The number of amastigotes/100 macrophages (No. A/100 Mø) is determined and the anti-amastigote activity expressed as (%AA): %AA=[1-(No. A/100 Mø)p/(No. A/100 Mø)c]×100

³H-Thymidine Incorporation Assay

A 200 µL MEM suspension containing a mammalian cell line such as U937 (human macrophage), J774 (mouse macrophage) or Vero (African green monkey kidney) cells is added to each well in 96 well flat-bottom microtitre plates and incubated for 24 to 48 h at 37° C. in 5% $CO_2$. The medium is removed and the cells washed three times in PBS. A 200 µL mixture of MEM containing 1×10⁷/ml stationary phase *T. cruzi* trypomastigotes is added to each well then incubated for 24 or 48 h under the same conditions. After the incubation period the media is removed and the cells washed three times in PBS. The test compounds in MEM are added to the appropriate wells and incubated for up to three days. At the end of the incubation period the media is removed and the cells washed three times in PBS and the macrophages lysed with 0.01% sodium dodecyl sulphate (SDS) and the parasitic cells harvested. The harvested parasitic cells are suspended in Grace's insect media and incubated at 28° C. for 48 h. At the end of the incubation period 1 µCi of ³H-thymidine in Grace's insect media is added to each well and incubated for an additional 20 h; this is harvested and ³H-thymidine incorporation is measured.

What is claimed is:

1. A compound of the following formula:

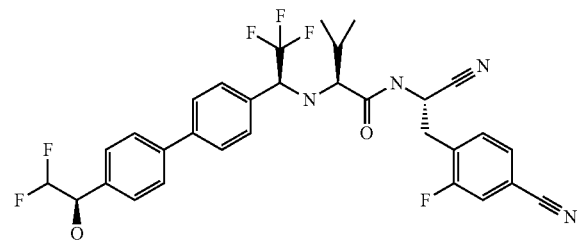 [SMILES: CC(C)[C@H](N[C@@H](c1ccc(-c2ccc([C@@H](O)C(F)F)cc2)cc1)C(F)(F)F)C(=O)N[C@H](C#N)Cc1ccc(C#N)cc1F]

or a pharmaceutically acceptable salt or stereoisomer thereof.

2. A pharmaceutical composition comprising a compound according to claim 1 and a pharmaceutically acceptable carrier.

3. A pharmaceutical composition of claim 2 further comprising another agent selected from the group consisting of: nifurtimox, benznidazole, allopurinol, terbinafine, lovastatin, ketoconazole, itraconazole, posaconazole, miltefosine, ilmofosine, pamidronate, alendronate, risedronate, chloroquine, proguanil, mefloquine, quinine, pyrimethamine-sulphadoxine, doxocycline, berberine, halofantrine, primaquine, atovaquone, pyrimethamine-dapsone, artemisinin, quinhaosu meglumine antimonite, sodium stibogluconate, amphotericin B, praziquantel, oxamniquine, pentamidine, melarsoprol, suramin and eflornithine and the pharmaceutically acceptable salts and mixtures thereof.

4. A method of treating a patient having a parasitic disease comprising administering to the patent in need thereof a composition comprising a compound of claim 1, wherein the parasitic disease is selected from the group consisting of toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis.

5. The method of claim 4 wherein the parasitic disease is Chagas disease.

6. The method of claim 4, wherein the composition further comprises a second agent selected from the group consisting of: nifurtimox, benznidazole, allopurinol, terbinafine, lovastatin, ketoconazole, itraconazole, posaconazole, miltefosine, ilmofosine, pamidronate, alendronate, risedronate, chloroquine, proguanil, mefloquine, quinine, pyrimethamine-sulphadoxine, doxocycline, berberine, halofantrine, primaquine, atovaquone, pyrimethamine-dapsone, artemisinin, quinhaosu, meglumine antimonite, sodium stibogluconate, amphotericin B, praziquantel, oxamniquine, pentamidine, melarsoprol, suramin and eflornithine and the pharmaceutically acceptable salts and mixtures thereof.

7. A compound of the formula selected from the following:

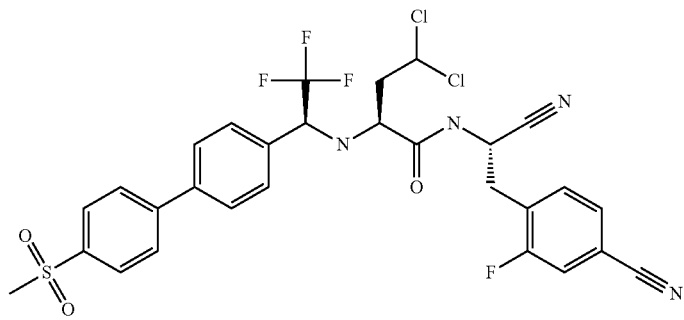 [SMILES: CS(=O)(=O)c1ccc(-c2ccc([C@H](N[C@@H](CC(Cl)Cl)C(=O)N[C@H](C#N)Cc3ccc(C#N)cc3F)C(F)(F)F)cc2)cc1]

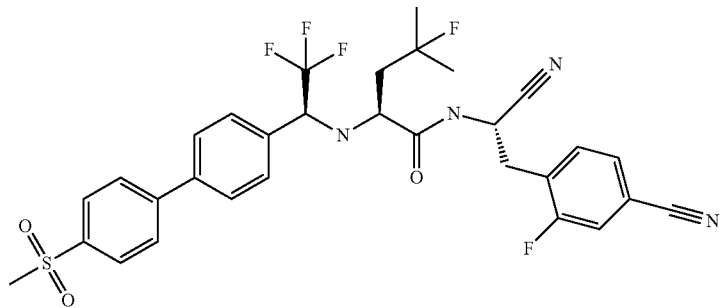

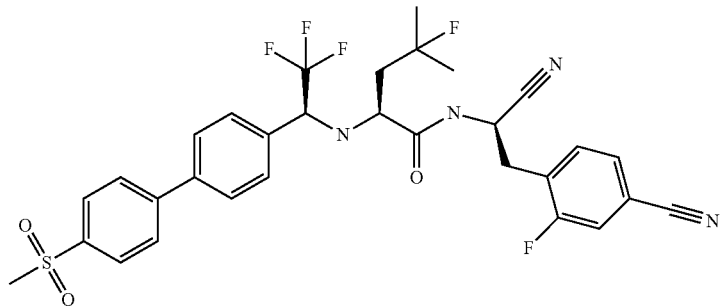 [SMILES: CC(C)(F)C[C@H](N[C@@H](c1ccc(-c2ccc(S(C)(=O)=O)cc2)cc1)C(F)(F)F)C(=O)N[C@@H](C#N)Cc1ccc(C#N)cc1F]

-continued
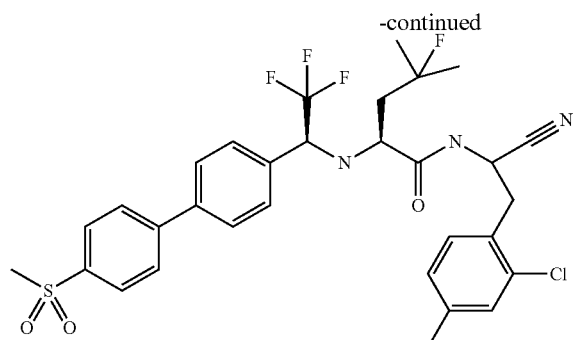
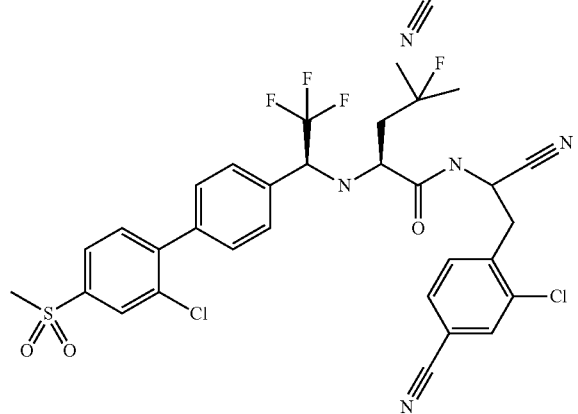
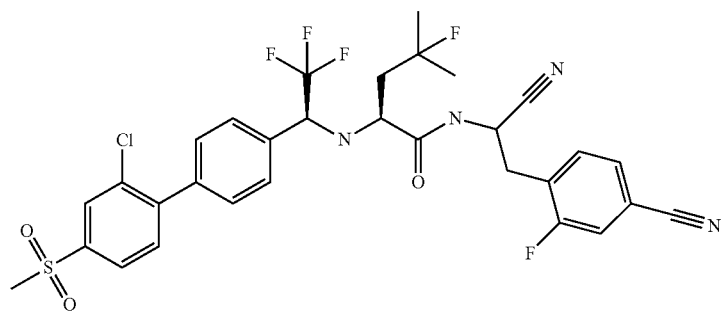 [SMILES: CC(C)(F)C[C@H](N[C@@H](c1ccc(-c2ccc(S(C)(=O)=O)cc2Cl)cc1)C(F)(F)F)C(=O)NC(C#N)Cc1ccc(C#N)cc1F]
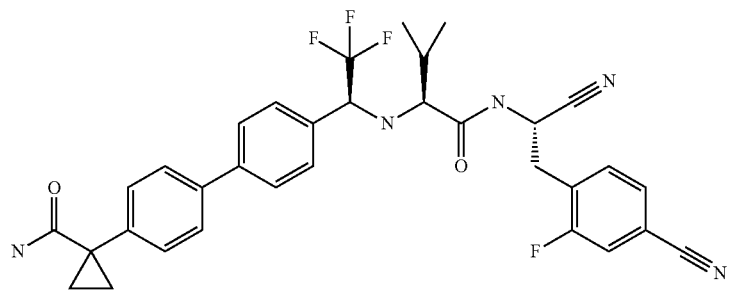 [SMILES: CC(C)[C@H](N[C@@H](c1ccc(-c2ccc(C3(C(N)=O)CC3)cc2)cc1)C(F)(F)F)C(=O)N[C@H](C#N)Cc1ccc(C#N)cc1F]
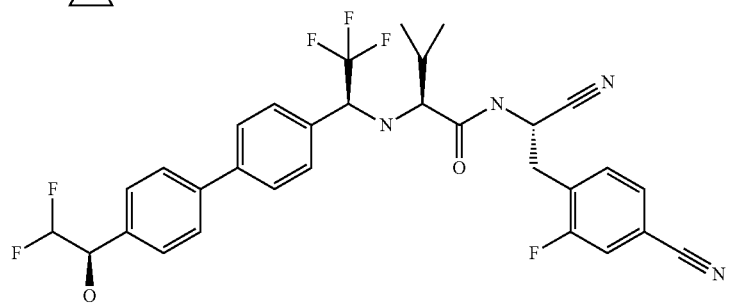

-continued
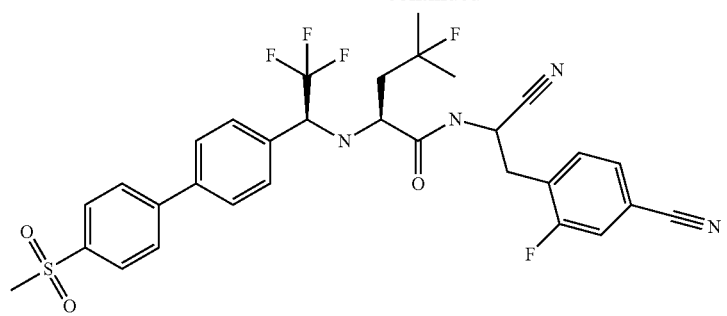 [SMILES: CC(C)(F)C[C@H](N[C@@H](c1ccc(-c2ccc(S(C)(=O)=O)cc2)cc1)C(F)(F)F)C(=O)NC(C#N)Cc1ccc(C#N)cc1F]
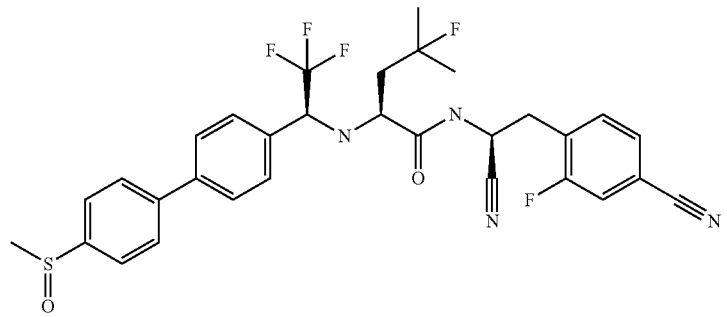 [SMILES: CS(=O)c1ccc(-c2ccc([C@H](N[C@@H](CC(C)(C)F)C(=O)N[C@H](C#N)Cc3ccc(C#N)cc3F)C(F)(F)F)cc2)cc1]
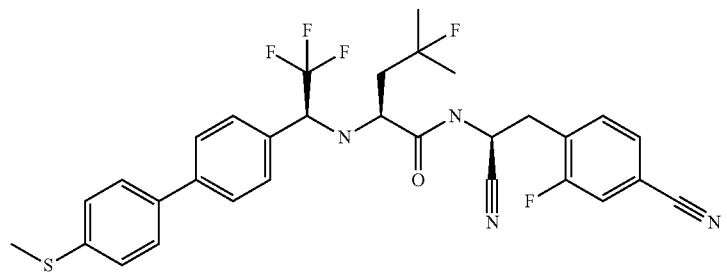 [SMILES: CSc1ccc(-c2ccc([C@H](N[C@@H](CC(C)(C)F)C(=O)N[C@H](C#N)Cc3ccc(C#N)cc3F)C(F)(F)F)cc2)cc1]
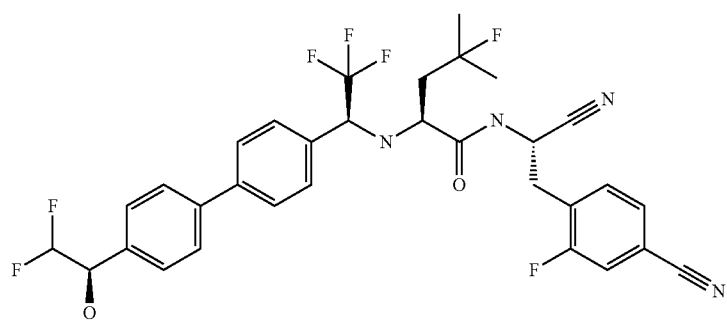 [SMILES: CC(C)(F)C[C@H](N[C@@H](c1ccc(-c2ccc([C@@H](O)C(F)F)cc2)cc1)C(F)(F)F)C(=O)N[C@H](C#N)Cc1ccc(C#N)cc1F]
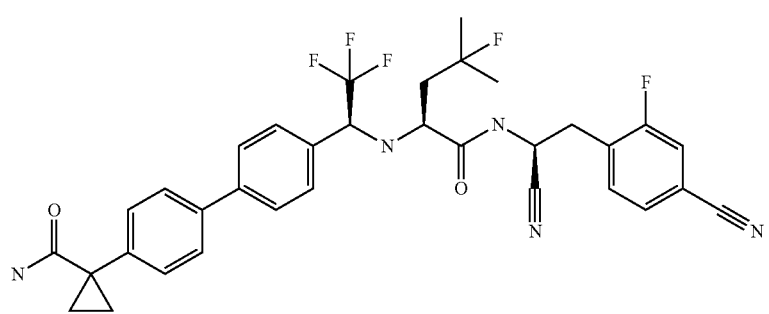 [SMILES: CC(C)(F)C[C@H](N[C@@H](c1ccc(-c2ccc(C3(C(N)=O)CC3)cc2)cc1)C(F)(F)F)C(=O)N[C@H](C#N)Cc1ccc(C#N)cc1F]

-continued
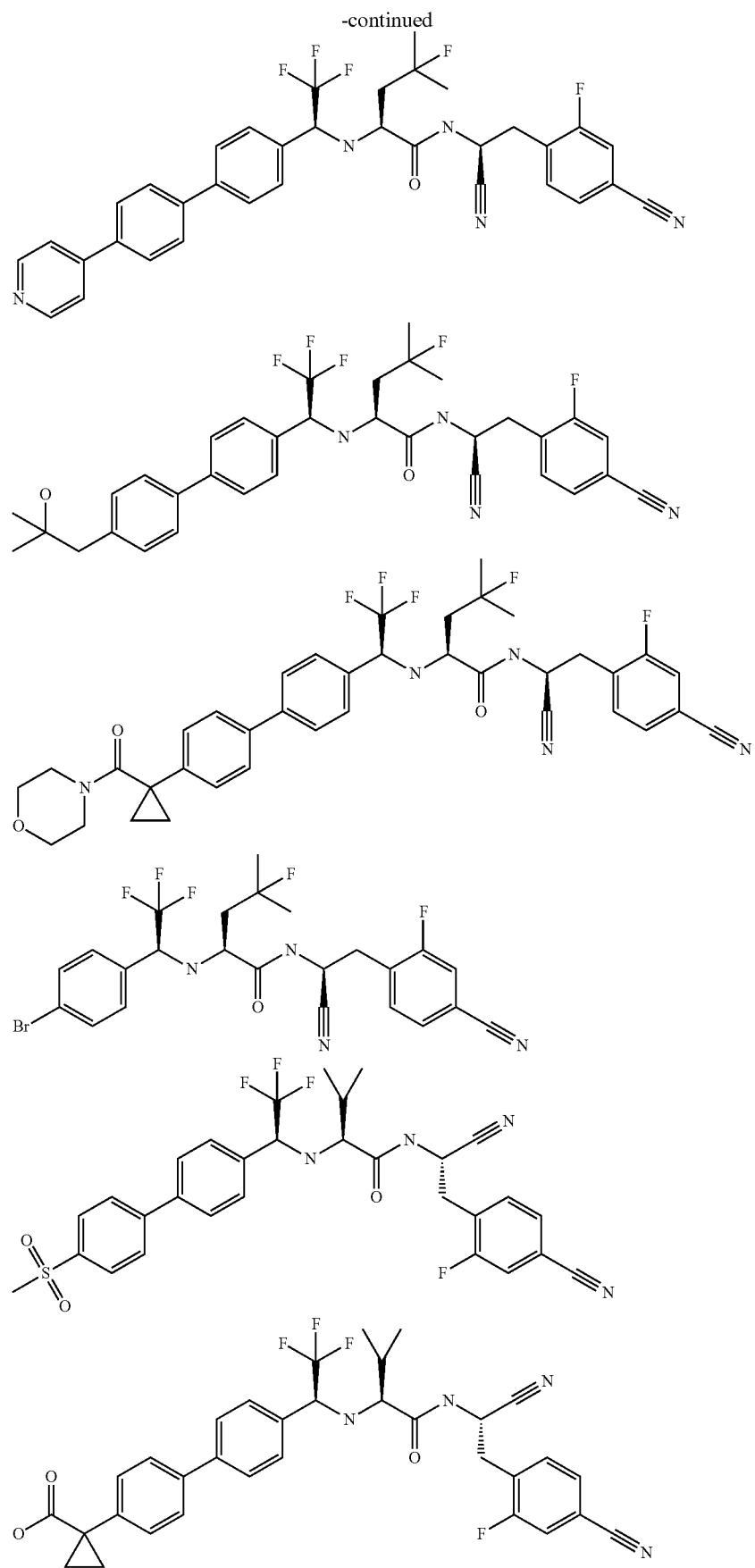

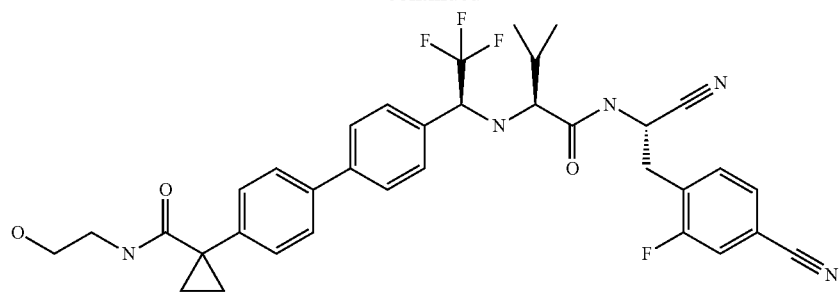 [SMILES: CC(C)[C@H](N[C@@H](c1ccc(-c2ccc(C3(C(=O)NCCO)CC3)cc2)cc1)C(F)(F)F)C(=O)N[C@H](C#N)Cc1ccc(C#N)cc1F]
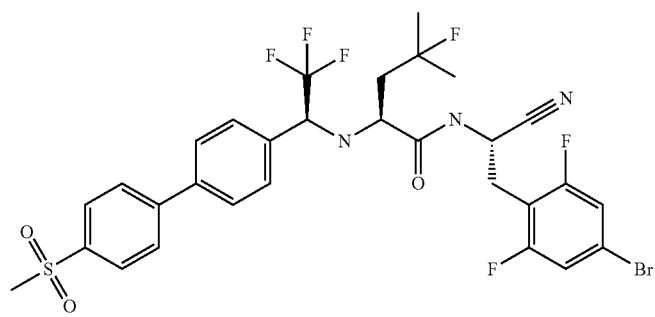 [SMILES: CC(C)(F)C[C@H](N[C@@H](c1ccc(-c2ccc(S(C)(=O)=O)cc2)cc1)C(F)(F)F)C(=O)N[C@H](C#N)Cc1c(F)cc(Br)cc1F]
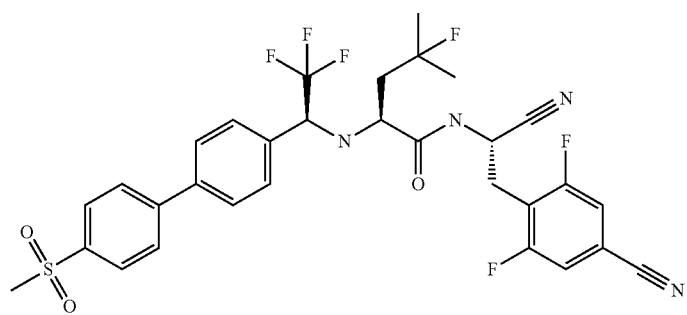 [SMILES: CC(C)(F)C[C@H](N[C@@H](c1ccc(-c2ccc(S(C)(=O)=O)cc2)cc1)C(F)(F)F)C(=O)N[C@H](C#N)Cc1c(F)cc(C#N)cc1F]
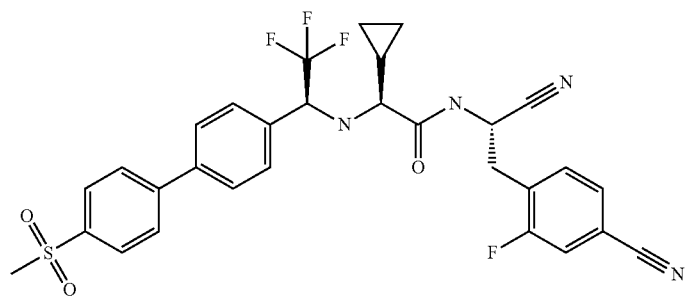 [SMILES: CS(=O)(=O)c1ccc(-c2ccc([C@H](N[C@H](C(=O)N[C@H](C#N)Cc3ccc(C#N)cc3F)C3CC3)C(F)(F)F)cc2)cc1]
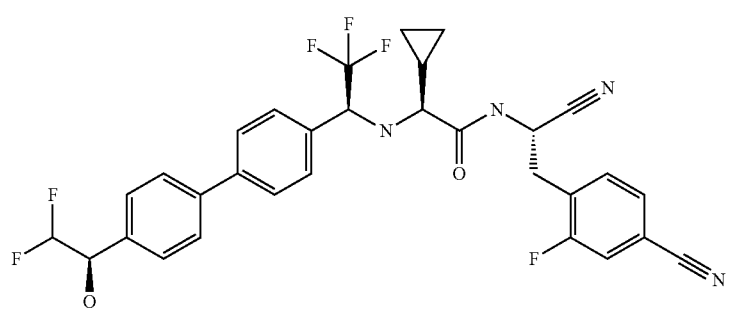 [SMILES: N#Cc1ccc(C[C@@H](C#N)NC(=O)[C@@H](N[C@@H](c2ccc(-c3ccc([C@@H](O)C(F)F)cc3)cc2)C(F)(F)F)C2CC2)c(F)c1]

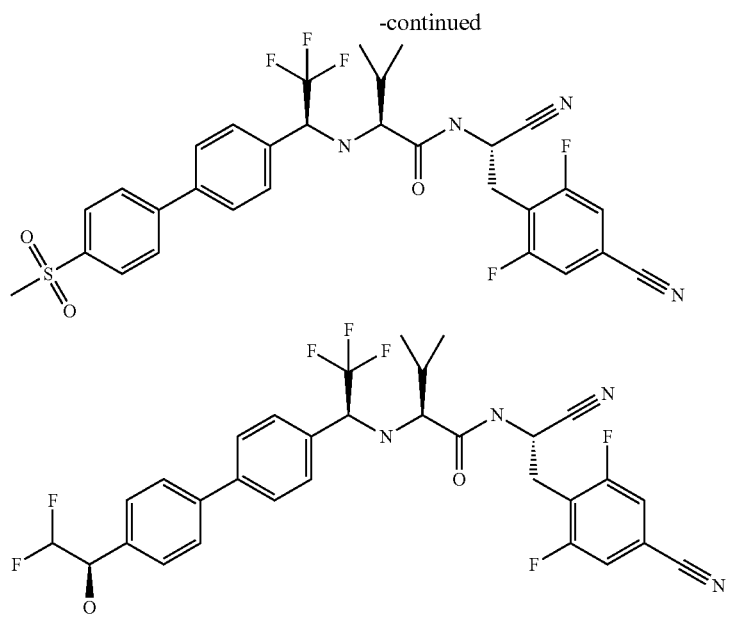

or a pharmaceutically acceptable salt or stereoisomer thereof.

8. A pharmaceutical composition comprising a compound according to claim 7 and a pharmaceutically acceptable carrier.

9. A pharmaceutical composition of claim 8 further comprising another agent selected from the group consisting of: nifurtimox, benznidazole, allopurinol, terbinafine, lovastatin, ketoconazole, itraconazole, posaconazole, miltefosine, ilmofosine, pamidronate, alendronate, risedronate, chloroquine, proguanil, mefloquine, quinine, pyrimethamine-sulphadoxine, doxocycline, berberine, halofantrine, primaquine, atovaquone, pyrimethamine-dapsone, artemisinin, quinhaosu meglumine antimonite, sodium stibogluconate, amphotericin B, praziquantel, oxamniquine, pentamidine, melarsoprol, suramin and eflornithine and the pharmaceutically acceptable salts and mixtures thereof.

10. A method of treating a patient having a parasitic disease comprising administering to the patent in need thereof a composition comprising a compound of claim 7, wherein the parasitic disease is selected from the group consisting of toxoplasmosis, malaria, African trypanosomiasis, Chagas disease, leishmaniasis, schistosomiasis, amebiasis, giardiasis, clonorchiasis, opisthorchiasis, paragonimiasis, fasciolopsiasis, lymphatic filariasis, onchocerciasis, dracunculiasis, *ascariasis*, trichuriasis, stronglyoidiasis, trichostrongyliasis, trichomoniasis and cestodiasis.

11. The method of claim 10 wherein the parasitic disease is Chagas disease.

12. The method of claim 11, wherein the composition further comprises a second agent selected from the group consisting of: nifurtimox, benznidazole, allopurinol, terbinafine, lovastatin, ketoconazole, itraconazole, posaconazole, miltefosine, ilmofosine, pamidronate, alendronate, risedronate, chloroquine, proguanil, mefloquine, quinine, pyrimethamine-sulphadoxine, doxocycline, berberine, halofantrine, primaquine, atovaquone, pyrimethamine-dapsone, artemisinin, quinhaosu, meglumine antimonite, sodium stibogluconate, amphotericin B, praziquantel, oxamniquine, pentamidine, melarsoprol, suramin and eflornithine and the pharmaceutically acceptable salts and mixtures thereof.

\* \* \* \* \*